US010119905B2

(12) United States Patent
Azizian

(10) Patent No.: US 10,119,905 B2
(45) Date of Patent: Nov. 6, 2018

(54) VERIFICATION OF OLIVE OIL COMPOSITION

(71) Applicant: Hormoz Azizian, Oakville (CA)

(72) Inventor: Hormoz Azizian, Oakville (CA)

(73) Assignee: NIR Technologies Inc., Oakville, ON (CA)

( * ) Notice: Subject to any disclaimer, the term of this patent is extended or adjusted under 35 U.S.C. 154(b) by 0 days.

(21) Appl. No.: 15/486,333

(22) Filed: Apr. 13, 2017

(65) Prior Publication Data

US 2017/0299506 A1  Oct. 19, 2017

Related U.S. Application Data

(60) Provisional application No. 62/324,060, filed on Apr. 18, 2016.

(51) Int. Cl.
| | |
|---|---|
| *G01J 5/02* | (2006.01) |
| *G01N 21/359* | (2014.01) |
| *G01N 21/3577* | (2014.01) |
| *G01N 33/03* | (2006.01) |
| G01N 21/35 | (2014.01) |

(52) U.S. Cl.
CPC ....... *G01N 21/359* (2013.01); *G01N 21/3577* (2013.01); *G01N 33/03* (2013.01); *G01N 2021/3595* (2013.01)

(58) Field of Classification Search
CPC ............... G01N 33/03; G01N 21/3577; G01N 2021/3595
USPC ................................................... 250/339.12
See application file for complete search history.

(56) References Cited

U.S. PATENT DOCUMENTS 7,288,768 B2    10/2007   Gore et al.

OTHER PUBLICATIONS

Opus Spectroscopy Software, User Manual, Version 6 (2006), p. 1-90, available at: http://files.nocnt.ru/hardware/science/senterra/opus65-doc-en/lab.pdf.*
Christy et al., "The Detection and Quantification of Adulteration in Olive Oil by Near-Infrared Spectroscopy and Chemometrics", Analytical Sciences. Jun. 2004, vol. 20, pp. 935-940.
Obeidat et al., "Classification of Edible Oils and Uncovering Adulteration of Virgin Olive Oil Using FTIR with the Aid of Chemometrics", Australian Journal of Basic and Applied Sciences, 2009, vol. 3(3), pp. 2048-2053.

(Continued)

*Primary Examiner* — Kenneth J Malkowski
(74) *Attorney, Agent, or Firm* — Manelli Selter PLLC; Edward J. Stemberger

(57) ABSTRACT

A new rapid Fourier transform near infrared (FT-NIR) spectroscopic method is described to screen for the authenticity of edible oils, and in particular, extra virgin olive oils (EVOO). To screen these oils, the samples to be tested are pre-classified into one of a series of classification groups using a suitable classification criteria, such as fatty acid (FA) content. As a result, the oils are classified into Groups having similar properties. FT-NIR partial least squares (PLS1) calibration models are prepared for each group, based on FT-NIR analysis of authentic oils, and oils spiked with a specific type and amount of an adulterant. Using these different PLS1 calibration models, a more rapid method for analyzing commercial extra virgin olive oils for adulteration is provided.

18 Claims, 12 Drawing Sheets

(56) References Cited

OTHER PUBLICATIONS

Rohman et al., "Fourier transform Infrared (FTIR) spectroscopy for analysis of extra virgin olive oil adulterated with palm oil", Food Research International, 2010, vol. 43, pp. 886-892.
Rohman et al., "The Use of FTIR Spectroscopy and Chemometrics for Rapid Authentication of Extra Virgin Olive Oil", J Am. Oil Chem. Soc., 2014, vol. 91, pp. 207-213.
Tay et al., "Authentication of Olive Oil Adulterated with vegetable oils using Fourier transform Infrared Spectroscopy", Lebensm-Wiss. U.-Technol. 2002, vol. 35, pp. 99-103.

* cited by examiner

Fig. 2A (Prior Art)
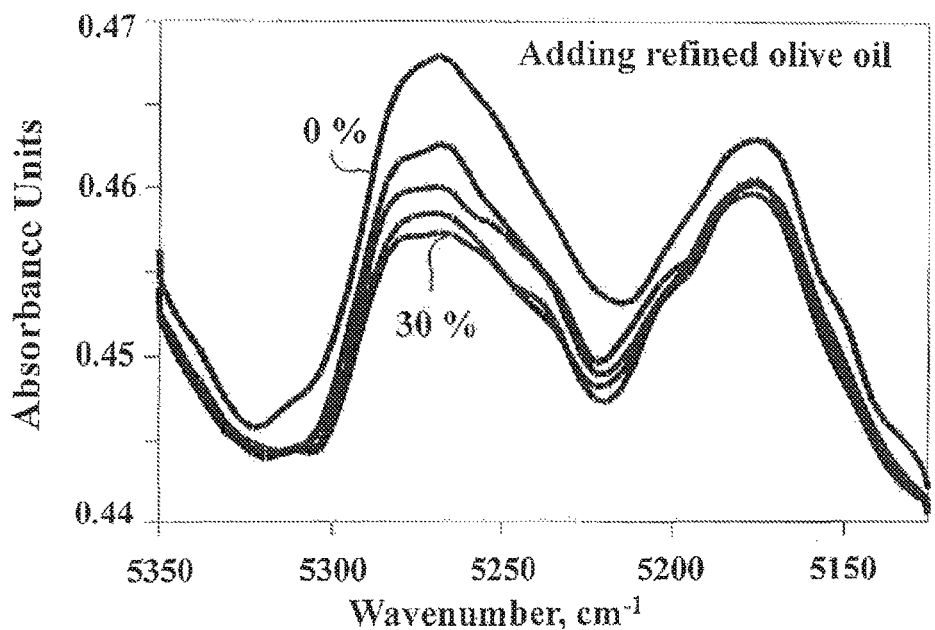
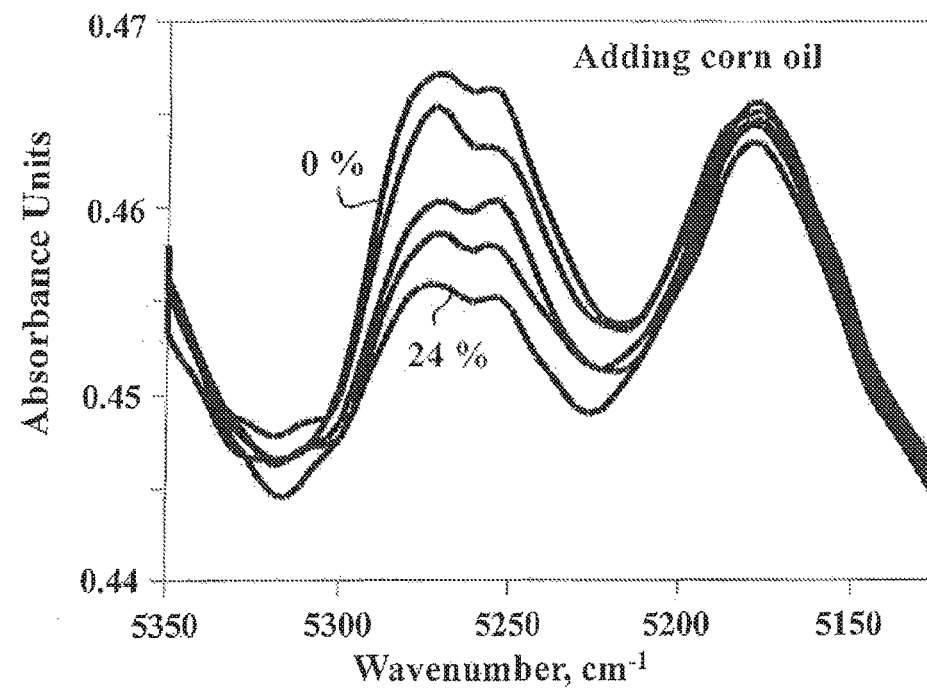
Fig. 2B (Prior Art)

VERIFICATION OF OLIVE OIL COMPOSITION

FIELD OF THE INVENTION

The present invention relates to a method for measuring the purity of a food product, and in particular, food oils, and the like. In its most preferred embodiment, the present invention relates to a method for the determination of the purity and freshness of olive oil samples, and in particular, extra virgin olive oil samples, using an FT-NIR spectroscopy based analytical technique.

BACKGROUND OF THE INVENTION

Establishing the authenticity of food products, and in particular, extra virgin olive oil (EVOO) continues to be of great interest to scientists and consumers, and detecting adulteration of EVOO for economic gain is an ongoing concern for regulatory agencies. Adulteration of EVOO, involving the replacement of high cost EVOO with lower grade and cheaper substitute oils can be very attractive and lucrative for a food manufacturer or raw material supplier. The adulteration of EVOO can also have major health implications to consumers. As such, the detection of EVOO adulteration is of importance.

There are many olive oil standards that have been approved and published by various associations and countries, which standards define grades of olive oils and specify chemical composition and quality parameters. These standards are regularly amended to accommodate the natural variations in olive oil cultivars and to upgrade them if new components are discovered in EVOO. These standards also typically include various recommended analytical techniques that can be used to verify the grade and quality of the oil being tested. In fact, a variety of prior art physical and chemical tests have been used to establish the authenticity of olive oil and to detect the level of adulterants in it.

Suggested techniques include the analysis of fatty acid profile of an oil, after methylation using gas chromatography (GC). High Performance Liquid Chromatography (HPLC) analysis of the fatty acid and triglycerides composition has also been studied. Further, approaches based on Nuclear Magnetic Resonance (NMR) analysis, or spectroflourometric methods have also been reported for detecting the adulteration of olive oil. However, many of these suggested methods used to detect adulteration of EVOO are labour intensive and/or are time consuming.

It should also be noted that previously, the desired development of a reliable and rapid method to detect adulteration of EVOO was found to be challenging and generally considered to be extremely difficult using a single analysis. Chemical methods combined with chromatographic separations of fatty acid methyl esters (FAME) or triacylglycerol (TAG) are only effective to detect the presence of added edible oils to EVOO products provided the composition of the adulterated oil mixture is sufficiently different from that of EVOO, i.e., contain higher FA levels of 18:2n-6, 18:3n-3, and 16:0, lower levels of 18:1n-9 and 16:0, or possess a different TAG structure compared to that of EVOO. In such cases, it might be possible to detect a 10 or 20% addition, but this approach has limited utility. For example, one could not detect the addition of a fully refined olive oil to an EVOO since both oils would have the same FA and TAG compositions.

UV spectroscopy based on 208-210 and 310-320 nm has also been widely used to detect the adulteration of extra virgin olive oil with refined olive oil. Unlike chromatographic procedures, vibrational spectroscopy techniques offers unique advantages because they are typically rapid, non-destructive, and can be applied to measure neat oils without any sample preparation or dilution in any solvent.

Similarly, mid-infrared (MIR) and near-infrared (NIR) spectroscopic techniques in conjunction with multivariate statistical methods have also been used to analyse and classify EVOO.

In our previous document, namely PCT Patent Application No. PCT/CA2016/000026, the contents of which are incorporated herewith in their entirety, we described an analytical technique for the detection of EVOO adulteration based on an FT-NIR analysis approach. In this approach, an FT-NIR calibration matrix (or model) was prepared based on analysis of known EVOO samples. The calibration matrix analysis included results from authentic EVOO samples, or EVOO samples spiked with various edible oils as adulterants, and additionally based on the results of a comparison of EVOO samples analysed by FT-NIR and also analysed by prior art analytical techniques (such as the results from GC analysis).

In this approach, the FT-NIR analysis can be used as a rapid method for the authentication of the various constituents of an EVOO sample. This includes the identification of the various constituent oils in the sample, and their respective concentrations.

Moreover, the purity of the oil sample, can be determined based on the spectral analysis of the sample oil at a specific frequency range, when compared to the value at this specific frequency range for an authentic oil. It was determined in PCT application No. PCT/CA2016/000026, that using an FT-NIR analysis conducted at a wave number centered at, or centered essentially at, around 5280 $cm^{-1}$, was preferred.

By using the phrase "essentially at", the skilled artisan will be aware that the band found at or near 5280 $cm^{-1}$, is to be analysed, and compared to a known EVOO spectrum. In actual fact, the levels found for this band can be analysed over a wave number range of about 5280+/−50 wave numbers. In any event, while there is some latitude in the exact wave number used, it was clear that the FT-NIR spectroscopy analysis peak centered at approximately 5280 $cm^{-1}$ is a FT-NIR spectroscopy peak which is of interest in determining the authenticity of an oil sample.

Further, in PCT/CA2016/000026, it was described that the results obtained in the region of essentially 5280 wave numbers, could be compared to the FT-NIR results obtained for the known sample, centered at a wave number of essentially 5180 wave numbers. Again, the term "essentially", is to be interpreted as the results obtained over a wave number range of about 5180+/−50 wave numbers. Comparison of the ratio of these two wave number results, at both 5180 and 5280 wave numbers, in an authentic EVOO sample, and the ratio of these two wave number results in an unknown sample, allowed the development of an "FT-NIR Index" value. This value is the area under the curve at essentially 5280 wave numbers, divided by the area under the curve at 5180 wave number, and normalized to a value of 100. As such, for an authentic EVOO sample, the FT-NIR Index value should be at or about 100 since the ratios of the two wave number results obtained for the sample and for the authentic EVOO standard, should be the same. Variations from this value indicate an increasing possibility of adulteration, or degradation of the olive oil being tested. Consequently, the FT-NIR Index is at its highest (e.g. typically 100) when authentic EVOO is tested. In actual testing, indices of over 80 are preferred, with levels of over 90, 95 or even more 99, being even more preferred. Once the index falls below these levels (and particularly below the lower levels), adulteration or degradation of the oil sample is to be suspected.

As a result, the previous approach provided a single screening method that would rapidly authenticate a wide variety of EVOO samples, determine the constituent elements of an oil sample, and, if present, identify the nature (identity) and concentration of an adulterant in the EVOO sample.

However, while the previous technique provided a valuable tool for the rapid analysis of a number of different EVOO samples, it has been noted that analysis of some samples could be enhanced to provide a better indicator of whether the sample has been adulterated or the like.

As such, providing an improved, and more robust, rapid analysis method for the authentication of the constituents of an EVOO sample would clearly be beneficial. This would be particularly advantageous if the analytical technique could be used to rapidly verify the authenticity of a wider range of EVOO samples in order to verify that they were essentially authentic EVOO.

As such, it would be advantageous to be able to provide an improved and more robust, rapid technique for determining whether an edible oil sample, and in particular an EVOO sample, had been adulterated, and if so, identify the type, nature, and/or amount of EVOO adulteration that had occurred.

SUMMARY OF THE INVENTION

Accordingly, it is a principal advantage of the present invention to provide a method based on FT-NIR spectroscopy to rapidly analyse an edible oil sample, and preferably an olive oil sample, and most preferably an Extra Virgin Olive Oil ("EVOO") sample, to determine whether the sample has degraded, or has been adulterated.

Moreover, it is a further advantage of the present invention to provide an FT-NIR spectroscopy based analytical technique of an edible oil, and preferably an olive oil, and most preferably an EVOO, which can identify the presence of an adulterant, and preferably also identify and quantify, the type and level of adulteration, present in the sample.

It is a still further advantage of the present invention to provide an FT-NIR spectroscopy based analytical technique which can identify and quantify at least 1 adulterant present in an olive oil sample, and preferably an EVOO sample. More preferably, the FT-NIR spectroscopy based analytical technique is one which can be used to identify between 1 and 6 adulterants, and preferably between 1 and 3 adulterants, present in the olive oil sample being analysed.

It is yet a still further advantage of the present invention to provide an FT-NIR spectroscopy based analytical technique which is more robust than previously described techniques, and which is capable of providing an improved analysis of a wider variety of oil samples, and in particular, EVOO samples, than the technique described in prior art techniques.

The advantages set out hereinabove, as well as other objects and goals inherent thereto, are at least partially or fully provided by the method of the present invention, as set out herein below.

Accordingly, in one aspect, the present invention provides a method for the detection of adulteration in a test edible oil sample, and preferably a test olive oil sample, and most preferably, a test EVOO sample, comprising:

establishing a series of edible oil classifications using a selection criteria;

preparing an FT-NIR calibration matrix, comprising a series of calibration models for at least two, and preferably all, of said series of edible oil classifications, based on FT-NIR analysis of authentic oils and authentic oils spiked with adulterants, for each classification;

preparing and analysing said test edible oil sample using a pre-selection technique in order to determine and preselect the most suitable edible oil classification, and thereby determine the most suitable calibration models, for that oil sample;

conducting an FT-NIR spectroscopy analysis of said test edible oil sample;

analysing the FT-NIR spectroscopy analysis of said test edible oil sample, at selected frequency ranges; and, comparing the FT-NIR spectroscopy analysis of said test edible oil sample, to said calibration models for said classification, at said selected frequency ranges, in order to determine whether said test edible oil sample had been adulterated.

Preferably, the test edible oil sample is olive oil, and most preferably, is an extra virgin olive oil.

Using the technique described in PCT/CA2016/000026, it was noted that it was difficult to establish a single FT-NIR calibration matrix capable of analysing a wide variety of edible oils. Since the spectrographic characteristics of natural oils, and in particular, EVOO oils, can vary depending on a variety of factors, it was difficult to establish a single calibration matrix that could analyse all samples, while still providing the desired degree of accuracy for the analysis. It has now been found that by use of a pre-selection approach, the edible oil sample can be first classified into a classification group, and then analysed using the most appropriate calibration models, for that classification group.

As a result, pre-selection or classification of the olive oil into classes or groups prior to FT-NIR analysis facilitates the selection of the most appropriate calibration models to be used for testing of the sample oil. Preferably, several different calibration models are developed for various different oil classifications, and the appropriate calibration models can be determined by using any suitable pre-selection protocol which protocol is capable of classifying the sample oil into its most appropriate class, prior to analysis of the FT-NIR results. The number of different analysis classes is preferably at least 2, and more preferably between 2 and 10 classes. More preferably, between 3 and 7 classes are developed, and most preferably, between 4 and 6 preselection classes are determined, each with their own calibration models.

Using the example of an unknown EVOO sample, preselection testing can be conducted based on a number of factors. These might include manual classification, various analytical techniques such as IR or GC analysis, FT-NIR analysis based on FA content such as level of 18:1 n-9, 18:2 n-6, 16:0 FAs, or the ratio of 18:1 n-9 to 18:2 n-6, or the like. However, one preferred pre-selection criteria approach is based on measurement of the level of 18:2n-6 fatty acid (FA) present in the sample oil. While the FA content of the oil sample can be tested using a number of techniques, the preferred approach contemplated in the present application, relies on an FT-NIR analysis of the 18:2n-6 level present in the test sample, and comparing this value to the 18:2n-6 FA level in a known sample. For example, the technique described in U.S. Pat. No. 7,329,547, might be used to determine the FA levels. Using this approach, the level of 18:2n-6 FA can be measured directly, and compared to similar, known samples.

In a preferred method, however, a commercial FT-NIR analysis comparison package, such as Bruker's OPUS IDENT-Factorization software package, available from Bruker Corporation, might also be used. The aim of an DENT factorization analysis is to determine the differences between a test spectrum and the spectra found in a reference library of sample spectra prepared based on analysis of authentic (unadulterated) edible oils, or more preferably, EVOO products. In a preferred approach, the IDENT program prepares a "Hit Quality" value for the test sample. This is done by comparing the spectra from the test sample to the spectra of known samples in order to determine the degree of similarity between the two spectra. Hit Quality is defined as a measure of the spectral distance between the spectrum measured for the unknown sample, and the spectrum measured for a known sample. For an exact match, the Hit Quality value would be 0 since there should be no differences in the spectra for the two samples.

In practise, for any unknown sample, the Hit Quality will vary based on its similarity to each of the known standards. The reference sample which provides the lowest value for Hit Quality will provide an indication of the preferred classification group so that the best calibration models can be selected for analysis of the unknown sample.

The calculated Hit Quality value can also be compared to a pre-selected "Threshold value" for any given sample, and if the "Hit Quality" value is lower than the "Threshold value", the test sample can be considered as similar enough to, or even identical to, the particular reference sample selected. However, any classification sample with a Hit Quality value less than the Threshold value might be used to determine the appropriate calibration model.

Preferred Threshold values are values less than 0.5, more preferably less than 0.2, and still more preferably, less than 0.1, using the IDENT software. For selection of the appropriate classification group, the Hit Quality value for the selected group is preferably the lowest High Quality value observed for any of the classification groups, and is preferably below the Threshold value. If no classification samples provide a Hit Quality value below the Threshold value, additional classification samples may be required to provide a full range of sample materials.

In general however, use of the IDENT-Factorization software, or other similar software packages, is known to those skilled in the art, and the use of these packages is outside of the scope of the present embodiment. For more information, additional details of this software package are provided in, for example, Bruker's OPUS Spectroscopy Software, Version 6, User's Manual (published by Bruker OPTIK GmbH; 2006).

In any case, in accordance with one preferred approach of the present invention, unknown EVOO test samples are tested using FT-NIR, in the pre-selection stage, against the IDENT reference library. The FT-NIR spectra measured is compared to the spectra of the reference samples in the reference library, and the reference sample having the closest spectra to the unknown sample, is determined, based on its similarity to the reference library spectra. With this information, the unknown sample can be assigned to the same classification group as the known sample. Once the most appropriate classification group has been determined, the calibration models prepared for that classification group is subsequently used in the FT-NIR analysis of the edible oil sample being tested. Thus, the most appropriate calibration models are used, for analysis of the unknown oil sample.

Numerous factors can influence the pre-selection classification of the edible oil, and these can include growing season conditions, harvesting and extraction methods, storage conditions and the like. However, for EVOO, in particular, it has now been noted that the variety of the olives used to prepare the oil can affect the content of various constituent oils within the olive oil. This provides a major, and somewhat unexpected, influence on the pre-selection of the appropriate oil classification. Fortunately, while there are literally hundreds of different varieties of olive oil, the number of pre-selection classifications can be limited to preferably between 4 and 6 different classifications, since it has been found that most varieties will fall within one of these classifications.

Accordingly, in the practise of the present invention, the edible oil can be analysed using the appropriate calibration models for that variety of oil, in order to best determine whether any adulteration or degradation of the oil, has taken place.

In a further aspect, once the test sample has been analysed, using the appropriate calibration models for that classification, and adulteration or degradation of the edible oil sample has been determined, the present invention also provides a method for the determination of the type and/or quantity of the level of adulteration in an adulterated edible oil sample, and preferably an adulterated olive oil sample, and most preferably, an adulterated EVOO sample. This method comprises:

establishing a series of edible oil classifications using a selection criteria;

preparing an FT-NIR calibration matrix, comprising a series of calibration models, for at least two, and preferably all, of said edible oil classifications, based on FT-NIR analysis of an authentic oil, and authentic oils which have been spiked with at least one, and preferably up to 4, and even more preferably up to 6 adulterants, for each classification;

preparing and analysing the edible oil sample in order to determine and pre-select the most suitable edible oil classification for that edible oil sample, and thereby determine the most suitable calibration models, for that oil;

analysing said adulterated edible oil using an FT-NIR spectroscopy based technique to produce an FT-NIR oil analysis;

comparing said FT-NIR oil analysis with said FT-NIR calibration models, in order to determine the type of oil, and the type of adulterant, and/or the level of adulterant present.

In a preferred approach, both the type and level of adulterant or adulterants, present in said sample, is determined.

Thus, preferably using the same FT-NIR spectra used to pre-select the classification group, and to determine adulteration, the FT-NIR spectroscopy result is then used for comparison to a calibration matrix that has been prepared based on the edible oil, and added adulterant. Calibration matrices can be prepared using the edible oil, and preferably, a selected EVOO, in combination with 1, 2, or more, adulterants, which are present at various levels. Using this analysis, the type and quantity of the adulterant(s) can be determined, and thus provide a qualitative and quantitative analysis of the sample to be tested.

In a preferred embodiment, the various calibration matrices for the different classifications can be prepared using various adulterants of interest, and these include those adulterants which are commonly added to EVOO. By way of example only, common adulterants include other natural edible oils, which typically include oils such as soybean oil, sunflower oil, corn oil, canola oil, hazelnut oil, high oleic acid safflower oil, peanut oil, palm olein oil, refined olive oil, caster seed oil, coconut, cotton seed oil, hemp oil, palm oil, palm kernel oil, poppy seed oil, rice bran oil safflower, sesame oil, and the like, and/or genetically modified oils, such as high oleic canola, high oleic sunflower, high oleic soybean, and the like.

Most typically, only one adulterant oil is added to an EVOO in order to prepare an adulterated oil. However, combinations of 2 or more adulterants can be added to adulterate an oil. Typically though, when adding a combination of adulterants, mixtures of less than 5 adulterants, and more typically less than 3 adulterants, are added to the EVOO.

DETAILED DESCRIPTION OF THE INVENTION

As background, it should also be noted that while there is no exact definition of the frequency range related to the term "near infrared" (NIR), generally, the term is used to define the range of frequencies between 4000 and 14000 $cm^{-1}$ wave number (2.5 to 0.71 microns), and the technique of the present invention is applicable over this general range. However, preferably, the FT-NIR technique of the present invention is practised within the range of 4300 to 9000 $cm^{-1}$ (2.33 to 1.11 microns), and even more preferably, the technique is practised within the range of 4500 to 7600 $cm^{-1}$ (2.22 and 1.32 microns).

Further, preparation of the calibration matrix is known to those skilled in the art, and may consist, at a simple level, as being a straight line comparison of the spectral data at a selected frequency to the spectral data obtained from the range of baseline materials. However, typically, the calibration matrix will be somewhat more complex mathematical model which can be used in order to compare a series of spectral data (e.g. frequency and transmittance and/or reflectance data). Using these mathematical models, a calibration matrix is prepared which is capable of determining the types and/or the amounts of a number of materials, such as fatty acids (FA) which may be present in a selected test material.

A calibration matrix will be prepared for at least two different classifications of oils.

The mathematical models used to prepare the various calibration matrices can be based on statistical analysis of the spectral data which have been compared to the other data, including gravimetric results, or results based on some other analytical technique, such as gas chromatography (GC), in order to analyse complex chemical mixtures and solutions.

Typically, the user will start by constructing a sample matrix of spectra for typical or authentic oils found in each classification group. As part of the pre-selection analysis, the FT-NIR spectra for the unknown sample is compared to the spectra for the typical or authentic oils, using the IDENT software, for example, in order to determine the typical or authentic oil spectra closest to spectra for the unknown sample. Once this has been established, the user will classify the unknown sample in the same classification group as the closest oil.

The user will also construct a data matrix from, for example, a comparison of the gravimetric or GC data, and the measured FT-NIR spectra, for a set of baseline materials, and grouped these together by classification group, using any suitable criteria (e.g. amount of 18:2n-6 FA levels). For each classification group, a calibration matrix is then prepared by mathematical analysis of the data matrix. Suitable mathematical approaches for preparation of each of the calibration matrices can include, for example, mathematical techniques such as multiple linear regression (MLR), principal component regression (PCR), and partial least squares regression (PLS), although other methods can be adopted. Preferably, a PLS-based method is used, and most preferably, the PLS-based method is a PLS1 method, which is a single variable PLS algorithm.

The pre-selection reference library for any given classification group can include a wide number of samples, or can be limited to only a few selected samples. For the latter approach, a less complex reference library is required. However, as more types of materials are analysed or otherwise encountered, with different fatty acid types and with wider ranges of fatty acid levels, the reference library will, by necessity become more complex. The skilled artisan, however, will be able to determine the complexity of the reference library required for the pre-selection operation.

The sample of the oil, and an EVOO in particular, is preferably pre-classified into any one of several classes using of the IDENT software package, in order to select an appropriate classification group, with its related PLS-based calibration matrix. However, as previously stated, other approaches for classification, if required, can be based simply on the 18:2n-6 FA content of the sample oil, or the like.

Still other approaches can be used. For example, if it is believed that oil to be tested is a known, specific variety, which has a known, specific classification group, the appropriate calibration models can be directly pre-selected by the user. However, preferably, the pre-selection classification is still routinely conducted using the FT-NIR results so that the pre-selection classification analysis confirms that the appropriate calibration matrix for that oil is selected.

It should also be noted that even though the proposed FT-NIR analyses and analytical techniques, are presented and discussed in several and separate sections, they are preferably viewed as, and conducted as, a single analysis. Thus, the measurement of the FT-NIR spectra for each unknown sample is only conducted once.

Moreover, each section of the analysis preferably addresses different approaches which are based on specific PLS calibration models that are applied to the same FT-NIR spectrum obtained from a given EVOO product or oil mixture. Typically, only when there is consistency between all sets of results, can one estimate with some confidence that a given test sample is authentic EVOO or a mixture of oils.

Further, it should also be noted that various techniques can be used to analyse the results obtained from the FT-NIR analysis. Generally it is expected that once an EVOO has been detected, and the appropriate classification selected, that an authentic EVOO will contain the full complement of numerous volatiles that give olive oils their characteristic aroma. Any reduction in these volatiles will reflect a decrease in the levels detected at or near the newly preferred absorbance band centered at essentially 5269 $cm^{-1}$ wave number, and thus, lower the FT-NIR Index, as previously described, based on these wave number values. As such, in this application, the technique of the present invention preferably also includes the determination of the FT-NIR Index for the sample material. As such, the present method preferably also includes an FT-NIR spectroscopy analysis which additionally comprises determining an FT-NIR Index for the sample to be tested, which FT-NIR Index is calculated by comparison of the changes in FT-NIR absorption at two different wave numbers ranges, and subsequently determining that said FT-NIR Index value is above an accepted value.

In this case, preferably the absorbance of the sample at essentially 5269 $cm^{-1}$ wave number is compared to the absorbance centered at essentially 5180 $cm^{-1}$ wave number and again normalized to 100. The phrase of "centered at essentially 5269 $cm^{-1}$ wave numbers", or "centered at essentially 5180 $cm^{-1}$ wave numbers", is again to be interpreted as the results obtained over a wave number range of +/−50 wave numbers, or the like. The skilled artisan will be aware that the wave number range selected will be appropriate for the peak characteristics of the peak being studied (e.g. broad, narrow etc.).

Variations from an FT-NIR Index value of 100, in an unknown sample being tested, indicate an increasing possibility of adulteration, or degradation of the olive oil being tested. In testing of unknown samples, indices of over 75 or 80 are preferred, with levels of over 90, 95 or even more than 99, being even more preferred. Once the index falls below these levels (and particularly below the lower levels), adulteration or degradation of the EVOO sample is to be suspected.

Once adulteration or degradation of an edible oil, and in particular, an EVOO, has been detected, or is suspected, based on the FT-NIR Index result, the pre-selection operation for the oil, can then be conducted, in order to identify the most appropriate classification group, and thus, the most appropriate calibration models. Accordingly, the method of the present invention preferably includes the step of determining the FT-NIR Index for the sample, prior to pre-selection of the classification group.

Further, once adulteration of the edible oil has been determined, the FT-NIR analysis can be conducted using the selected, and most appropriate, calibration models for that classification group. This allows the user to identify the type and amount of any adulterant present in an tested edible oil sample, and in particular, an EVOO product.

The FT-NIR protocol presented herein is unique since it provides at least two different calibration models for analysis of the FT-NIR spectrum of a given test oil, and the technique selects the most appropriate calibration models. As such, the present invention provides a more robust analytical technique which can more accurately analyse a wider range of edible oil products, and EVOO's in particular. While one could arrive at the same conclusions by using several different prior art analytical techniques, that process would be labour intensive and require expertise in a number of areas. On the other hand, the FT-NIR approach, including the determination of the FT-NIR Index, the classification step, and the PLS1 analytical methodology described herein, is relatively rapid and non-destructive, and provides the needed information on possible adulteration in minutes.

Furthermore, all of this information is preferably obtained from a single FT-NIR measurement using first the FT-NIR Index, and then classifying the oil using appropriately developed IDENT classification software. After classification has been completed, then PLS1-based analysis from the appropriate calibration models for the selected classification group, is conducted. Moreover, if adulteration is suspected, determination of the adulterant type and adulterant amount can be determined using additional PLS1-based analysis.

As such, the various features of novelty which characterize the invention are pointed out in the following discussion and examples. For a better understanding of the invention, its operating advantages and specific objects attained by its use, reference should be made to the accompanying tables, drawings, examples, and descriptive matter in which there are illustrated and described preferred embodiments of the invention.

EXAMPLES

The novel features which are believed to be characteristic of the present invention, as to its structure, organization, use and method of operation, together with further objectives and advantages thereof, will be better understood from the following examples in which presently preferred embodiments of the invention will now be illustrated by way of example only.

It is expressly understood, however, that the examples are for the purpose of illustration and description only and are not intended as a definition of the limits of the invention.

Moreover, it will be noted that for brevity, analysis of an EVOO sample is described in the following examples. However, the technique used and described is equally applicable to any edible oil, and preferably, any olive oil sample.

BRIEF DESCRIPTION OF THE DRAWINGS

Analysis of the following experimental results is augmented by the data presented in the accompanying drawings in which:

FIGS. 2a and 2b are prior art spectrums showing a reduction of band intensity near 5269 $cm^{-1}$ in EVOO as a result of mixing with either refined olive oil (FIG. 2a) or with refined corn oil (FIG. 2b);

MATERIALS AND METHODS

In this evaluation of EVOO, various reference olive oils were obtained from different sources, and tested using the method of the present invention. During testing, all spectra were obtained using Bruker Optics (Billerica, Mass., USA) FT-NIR spectrometers, model Matrix F or MPA, equipped with a diffuse reflection fiber optic probe and with a liquid attachment.

All PLS1 calibration models used or described herein, were generated by NIR Technologies Inc., Oakville, Ontario, Canada, by using Bruker OPUS software. All spectra were collected at room temperature using 8 $cm^{-1}$ resolution and the Blackman-Harris 3-term apodization function. Test oils were placed in 10-ml custom-made non-disposable test tubes designed to fit the FT-NIR probe attachment. Using this approach, the absorption spectra for each sample, was collected.

For each test, six replicate absorption spectra were measured, and these spectra were used to generate an average spectrum. The collected spectra were then used in the development of PLS1 calibration models, for the determination of FT-NIR Index values, for determination of the FA composition, for classification of the oil sample into an appropriate group, for determining the oil sample variety and/or for determining the adulterant type and concentration in adulterated EVOO samples.

Results

Determining the FT-NIR Index Value

Figure 1:
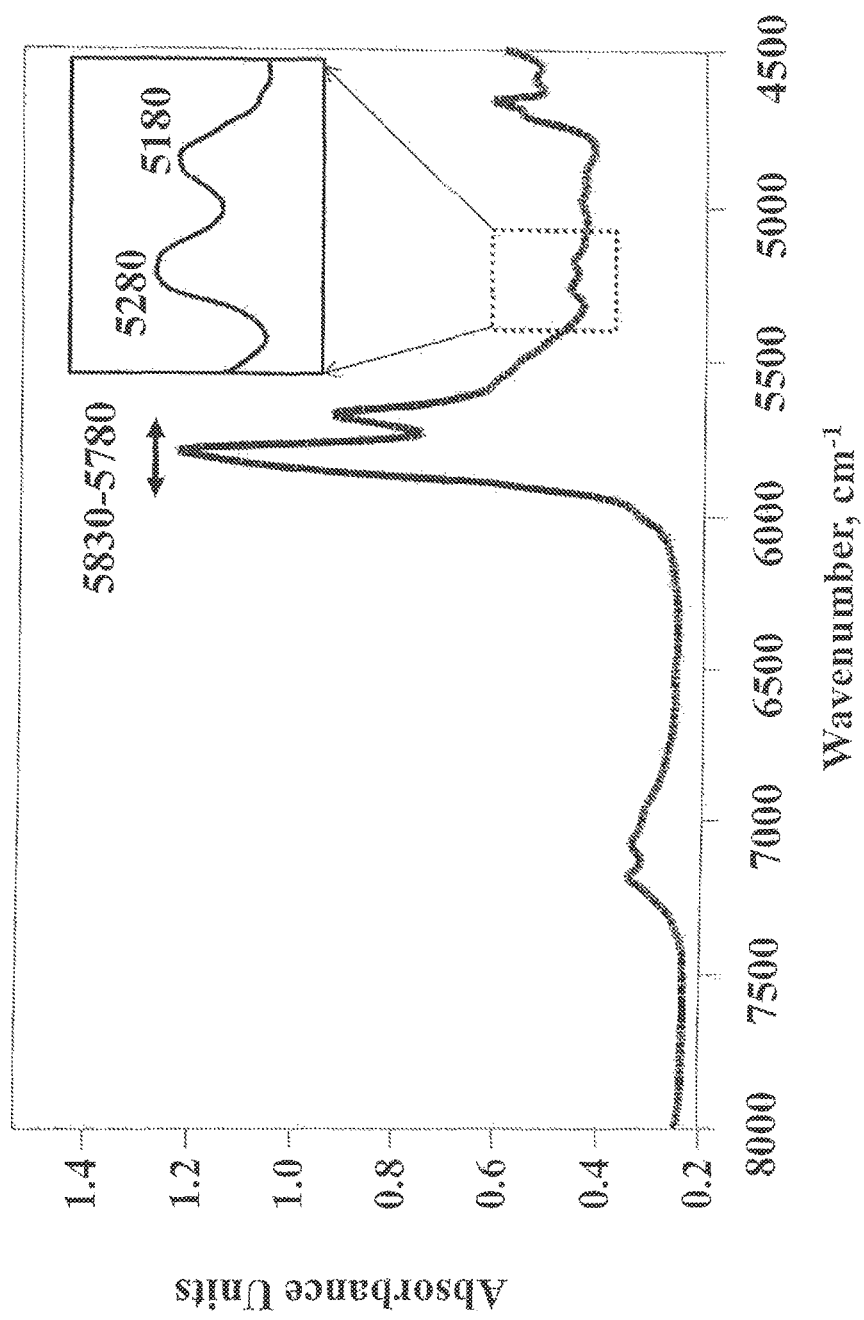
FIG. 1 is a prior art FT-NIR absorption spectrum of extra virgin olive oil showing the presence of bands at 5180 and 5269 $cm^{-1}$.

In the present study, the authenticity of selected samples of EVOO were evaluated after generating an FT-NIR Index PLS1 calibration model primarily based on the two weak, but highly characteristic FT-NIR absorption bands centered at, or near, 5180 and 5269 $cm^{-1}$. These two absorption band areas are in the carbonyl overtone region of the FT-NIR spectrum, and are shown in FIG. 1. The band centered at 5269 $cm^{-1}$ is mainly attributed to volatile compounds with carbonyl functional groups such as aldehydes, while the absorption band centered near 5180 $cm^{-1}$ consists of non-volatile carbonyl type compounds or esters. It is well known that volatile compounds are present in EVOO, and preliminary investigations of the volatile compounds in EVOO using gas chromatography/mass spectrometry (GC/MS) showed the presence of numerous aldehydes and other carbonyl-containing constituents.

In general, it has been found that the intensity of the band centered at 5269 $cm^{-1}$ in an authentic EVOO is relatively greater than the intensity of the band centered at 5180 $cm^{-1}$. However, when adulterants are added, by addition of for example, other edible oils, such as corn oil, or by addition of a fully refined olive oil, the absorption band centered at 5269 $cm^{-1}$ is still present, but at a lower intensity value relative to the absorption band centered at 5180 $cm^{-1}$. As such, addition of an adulterant oil to an EVOO results in a decrease in the absorption centered at 5269 $cm^{-}$. Characteristic decreases in the band intensity centered at essentially 5269 $cm^{-1}$ are shown in FIG. 2a for the addition of various amounts of refined olive oil, and in FIG. 2b for the additional of various amounts of added corn oil. As can be clearly seen, the intensity of the band centered at essentially 5269 $cm^{-1}$ is reduced by adding additional adulterant.

However, it will also be noted that the intensity of the second band near 5180 $cm^{-1}$ does not change significantly under any of these conditions and is similar for both the authentic EVOO and for the adulterated oils. The ratio of these two absorption bands (5269 $cm^{-1}$/5180 $cm^{-1}$) was used in the development of a the FT-NIR Index for any given edible oil sample, including EVOO samples.

It should be noted that other absorption bands might also be used for the determination of the FT-NIR Index. In the present application though, using these two absorption bands was found to be particularly useful in determining the FT-NIR Index value. As such, use of these two absorption bands is the preferred approach for determination of the FT-NIR Index.

The value of the FT-NIR Index is preferably calculated by using the following formula:

$$\text{FT-NIR Index} = [(\text{TS-ABS}_{5269}/\text{TS-ABS}_{5180})/(\text{Authentic-ABS}_{5269}/\text{Authentic-ABS}_{5180})] \times 100$$

Where: TS-ABS is the absorbance for the test sample in the range centered at essentially the indicated wave numbers; and Authentic-ABS is the absorbance for the authentic EVOO sample in the range centered at essentially the indicated wave number values.

While the FT-NIR index value provides some information, it is primarily a first screening tool that reflects the status of any edible oil at the time of measurement. It does not provide any information on the prior history of the oil and/or establish whether it was previously heated, refined, oxidized, or adulterated by being mixed with other oils. Generally though, identification of an oil with an FT-NIR Index value of less than 75 or 80 would certainly suggest that further investigation of the oil sample composition would be warranted.

Group Classification

It is known in the art that various edible oils contain variety amounts of different fatty acids (FA). In Table 1, the FA compositions of different plant oils, including EVOO, are shown. However, the levels of the FA for each type of plant oil can vary depending on various conditions including the plant variety.

A study therefore undertaken using a wide variety of EVOO samples, and as a result of this expanded study, the need to develop a pre-selection approach to EVOO analysis which divides the EVOO samples into various Groups or classes, was identified.

EVOOs typically found in North America, have a fairly common FA profile (e.g. about 70% 18:1n-9, 10% 18:2n-6, 0.7% 18:3n-3, 12% 16:0 and 3% 18:0). However, there are many other varieties of olive oils having markedly different FA profiles as evidenced by the FA ranges reported by, for example, the International Olive Council (IOC), and the like. For example, it was found that the variety of olive can influence the FA composition of the EVOO, and this would affect the preferred PLS1 calibration models to be used for that variety of EVOO.

There are many different olive oil varieties however, and the EVOO to be tested can include oils from many different olive varieties, or blends of two or three varieties of EVOOs. These varieties of oil include, but are not limited to, oils from Arbequina, Arbosana, Cerasuola, Cobrancosa, Cordovil, Frantoio, Hojiblanca, Koroneiki, Leccino, Mandural, Moraiolo, Nocella del Belice, Nostrane, Ogliarola and Picual olives, although other varieties of olives are not excluded. While there are numerous olive oil varieties, similar varieties typically tend to display the same grouping, regardless of source (e.g. country or region of origin), as discussed hereinbelow.

With this wider range of oils to be tested, with different FA compositions, it was determined that the use of a pre-selection approach, wherein the oils are first classified into different Groups or classes prior to selection of the appropriate FT-NIR PLS1 calibration model(s) to be used, would be of benefit.

Figure 3:
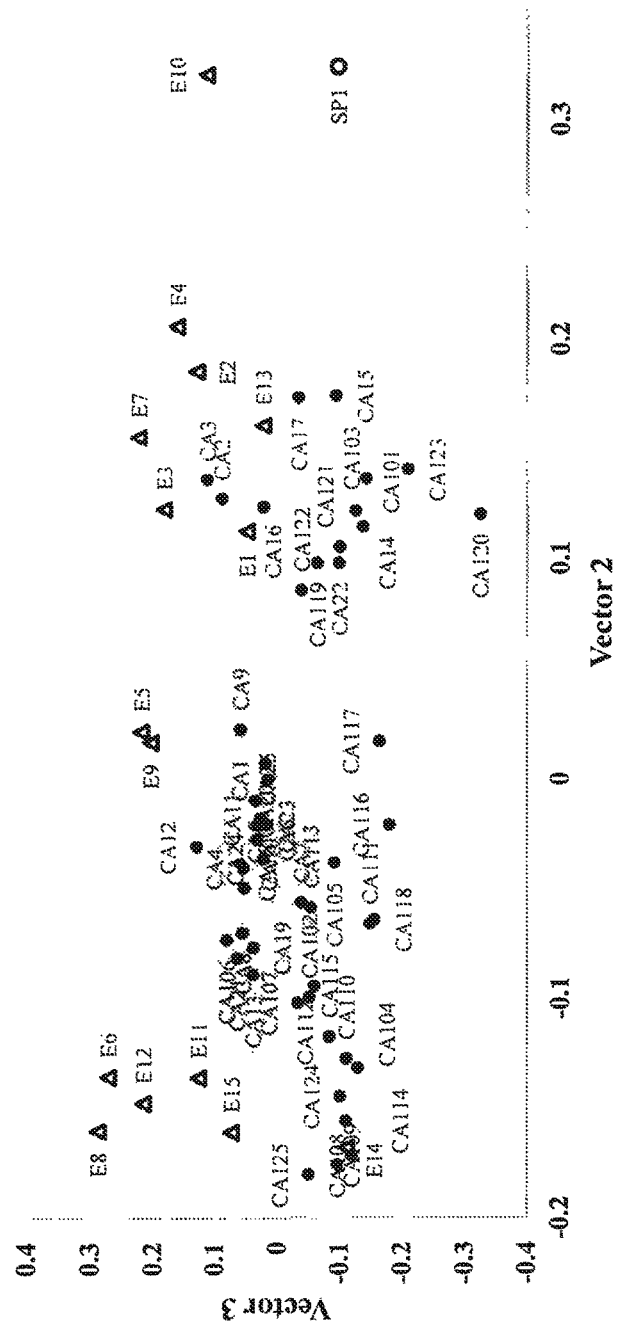
FIG. 3 shows a principle component analysis of Vector 2 versus Vector 3, for a variety of olive oil reference samples.
Figure 4:
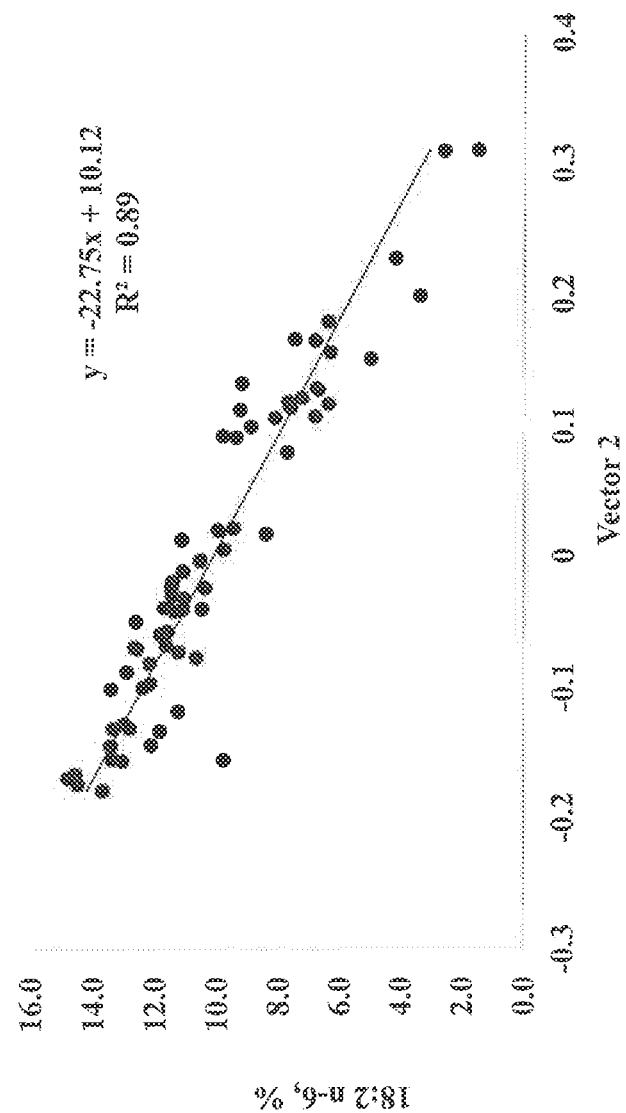
FIG. 4 shows the correlation of Vector 2 to the 18:2n-6 FA, for a variety of olive oil reference samples.
Figure 5:
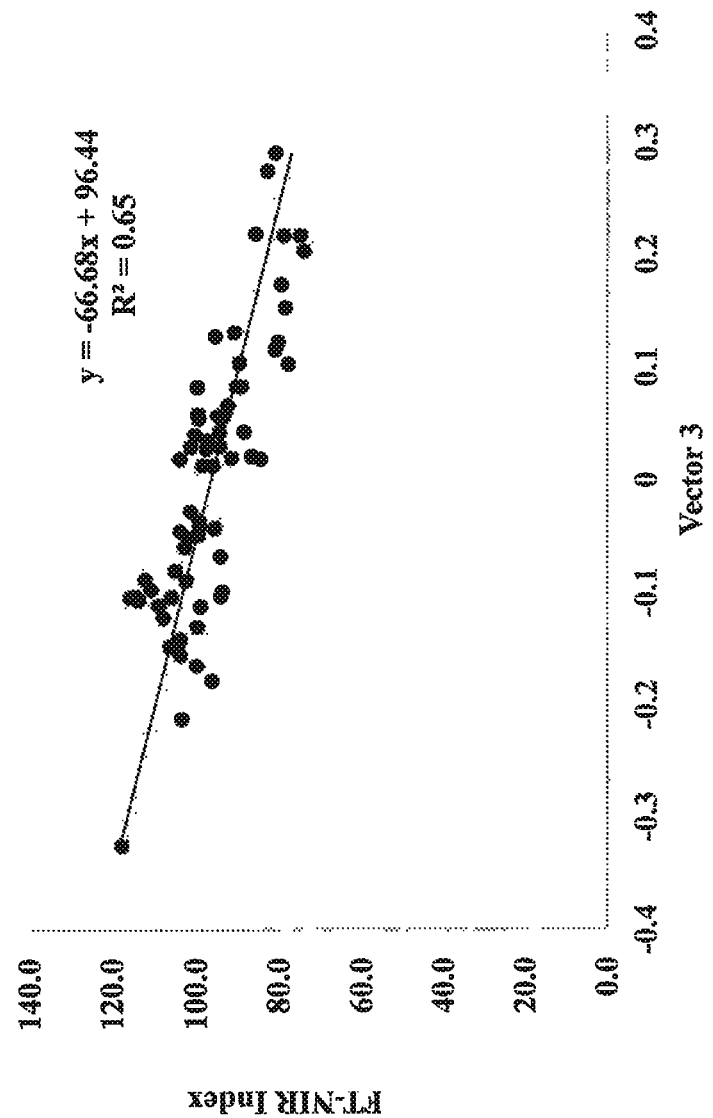
FIG. 5 shows the correlation of Vector 3 to the FT-NIR Index, for a variety of olive oil reference samples.

As such, a number of different authentic EVOO samples were tested. Some of these samples were from California, various Mediterranean countries, and one was from Spain, having a particularly low 18:2 n-6 content. No identifiable clusters in the principle component analysis (PCA) scores plotted for Vectors 2 or 3 (as shown in FIG. 3) were found. However, Vector 2 showed a high correlation to the content of LA (FIG. 4) and Vector 3 showed a high correlation to the FT-NIR Index (FIG. 5).

Figure 6A:
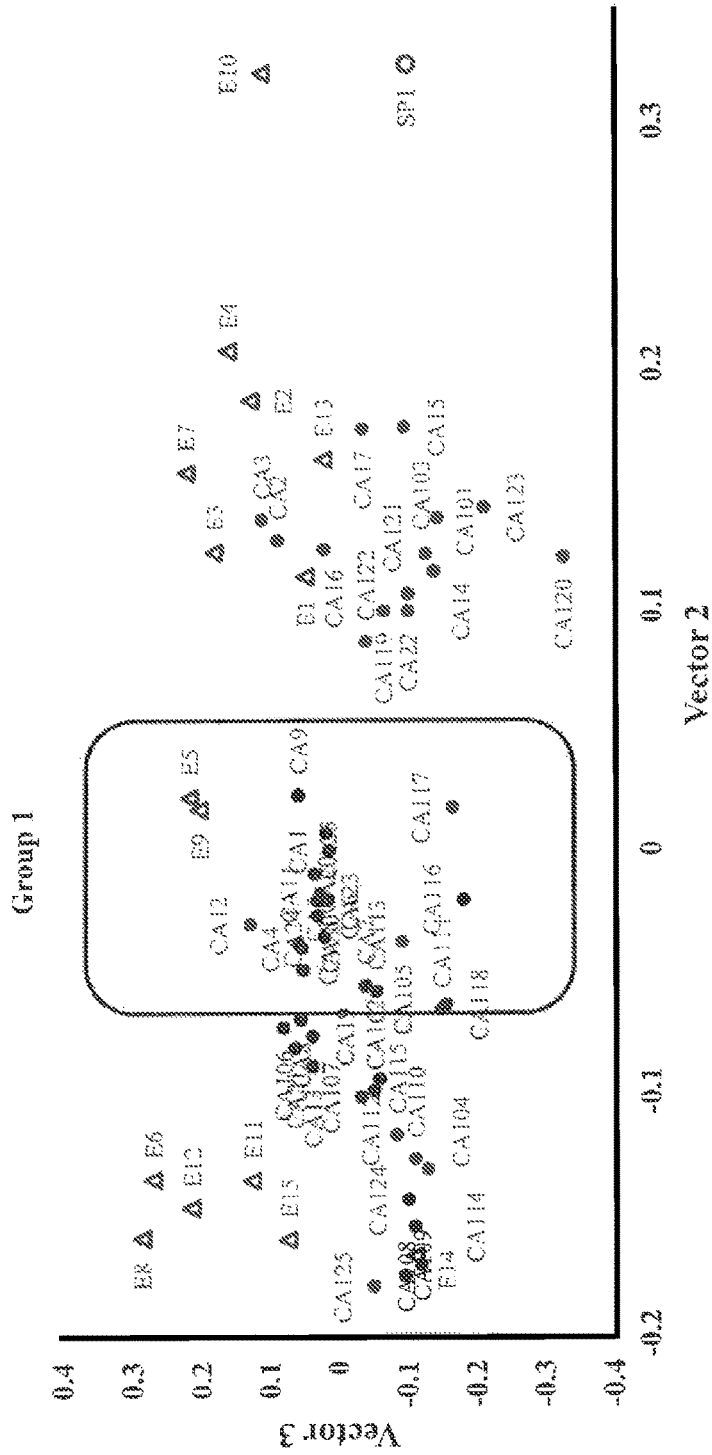
FIGS. 6A to 6D show the graph of FIG. 3, divided into 4 different IDENT groups (or classification groups)

These oils were analyzed using the previously developed PLS1 calibration models prepared and described in PCT/CA2016/000026, for different gravimetrically prepared mixtures of EVOOs spiked with adulterant oils high in linoleic acid (LA) such as corn oil, soybean oil, sunflower oil, canola oil, or the like, or high in oleic acid (OA) such as hazelnut oil, high oleic safflower, high oleic canola, high oleic sunflower, peanut oil, or the like, or high in palmitic acid (PO)

such as palm olein, or refined olive oil (RO). While it was observed that a number of EVOO products met the authenticity requirements of the previously described PLS1 calibration models, by yielding the expected low predicted values for LA, OA, PO, and RO, other authentic samples did not. Based on this outcome, this cluster of authentic products shown as being authentic was termed as Group 1, and this grouping is shown in FIG. 6A.

In assessing the FA composition of Group 1 EVOOs it was noted that the 18:2n-6 content in these samples was generally between 9.5% and 12.7%, which was consistent with the 18:2 n-6 content of the EVOO reference samples (9.5% to 11%) that were used in examples described in PCT/CA2016/000026, and thus, the development of the previous set of PLS1 calibration models. It was also noted that this range was a fairly narrow range for the range of 18:2 n-6 FA which might be found in EVOOs, when compared to all of the acceptable olive oil FA values (from 3.5% to 21%) which might be possible, according to the IOC.

Figure 6B:
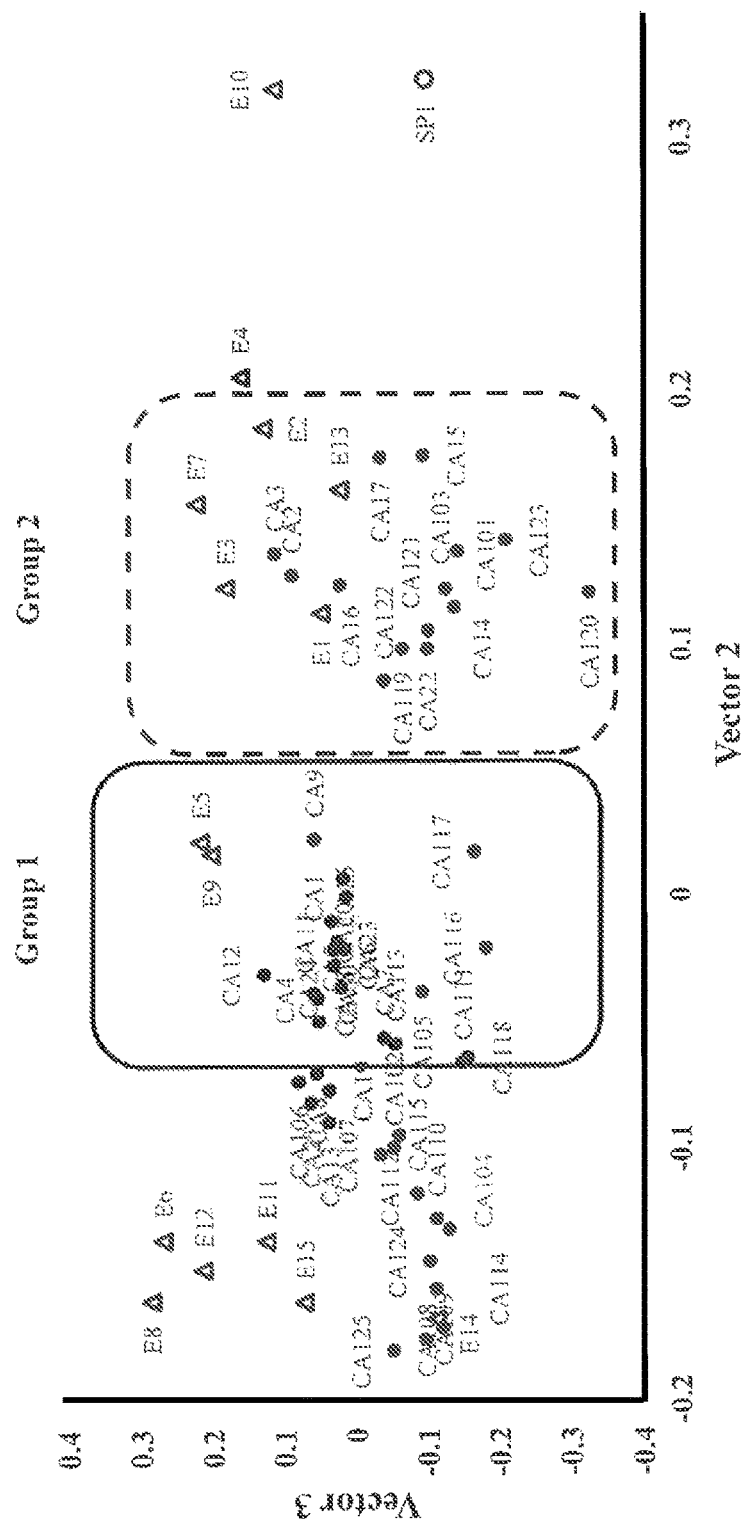

It was also noted that many of the remaining authentic EVOO samples were predicted to have high positive values for PO and negative values for LA and OA, according to the previous calibration models, which would suggest that these authentic products were adulterated with PO. This apparent adulteration of EVOO with PO was not expected, since it was believed that these samples were authentic, unadulterated EVOOs received directly from the producers. When the FA composition of these EVOOs was examined, it was noted that these EVOOs fell in a different range of 18:2n-6 of between 5.0% and 9.9%. This collection was then grouped together as Group 2 oils, as shown in FIG. 6B. A separate set of new PLS1 calibration models for this group of EVOO samples, was prepared, and using these PLS1 calibration models for the Group 2 EVOOs, low prediction values for LA, OA, PO, and RO, were achieved. This result was expected since a more representative set of PLS1 calibration models for this Group, was now being used.

Figure 6C:
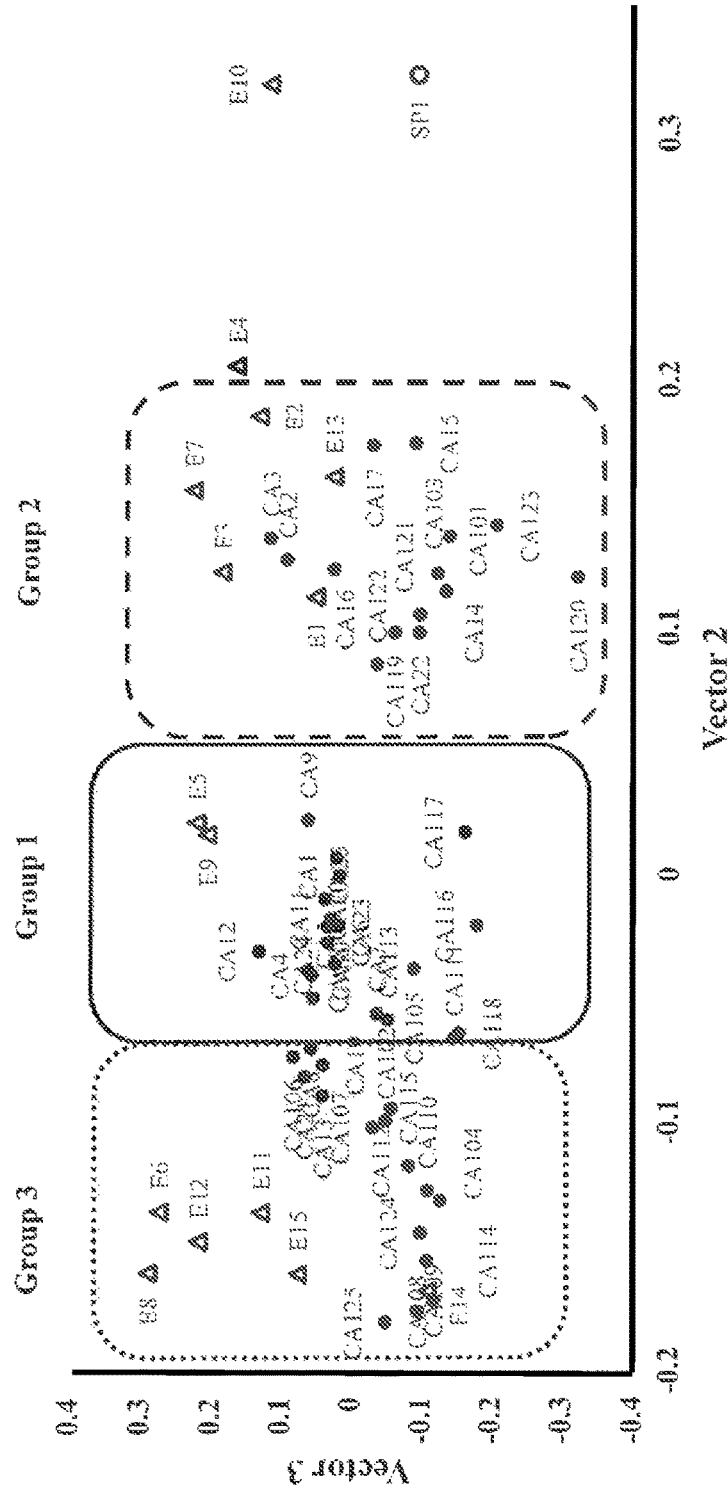

Similarly, in contrast to Group 2 oils that predicted positive PO values using the previously published PLS1 calibration models, a third group among the remaining EVOOs was observed that yielded a fairly high negative predicted value for PO and positive values for LA and OA. This selection of EVOOs had an 18:2n-6 content that fell in the range between 10.7% and 14.8%. This range was even higher than the one observed for Group 1 oils (9.5% to 12.7%). These oils were grouped together in a third group (Group 3), as shown in FIG. 6C. Again, a new separate set of PLS1 calibration models was prepared for this group of oils, and the new calibration models for Group 3 indeed predicted low values for LA, OA, PO, and RO for each of these EVOOs.

Figure 6D:
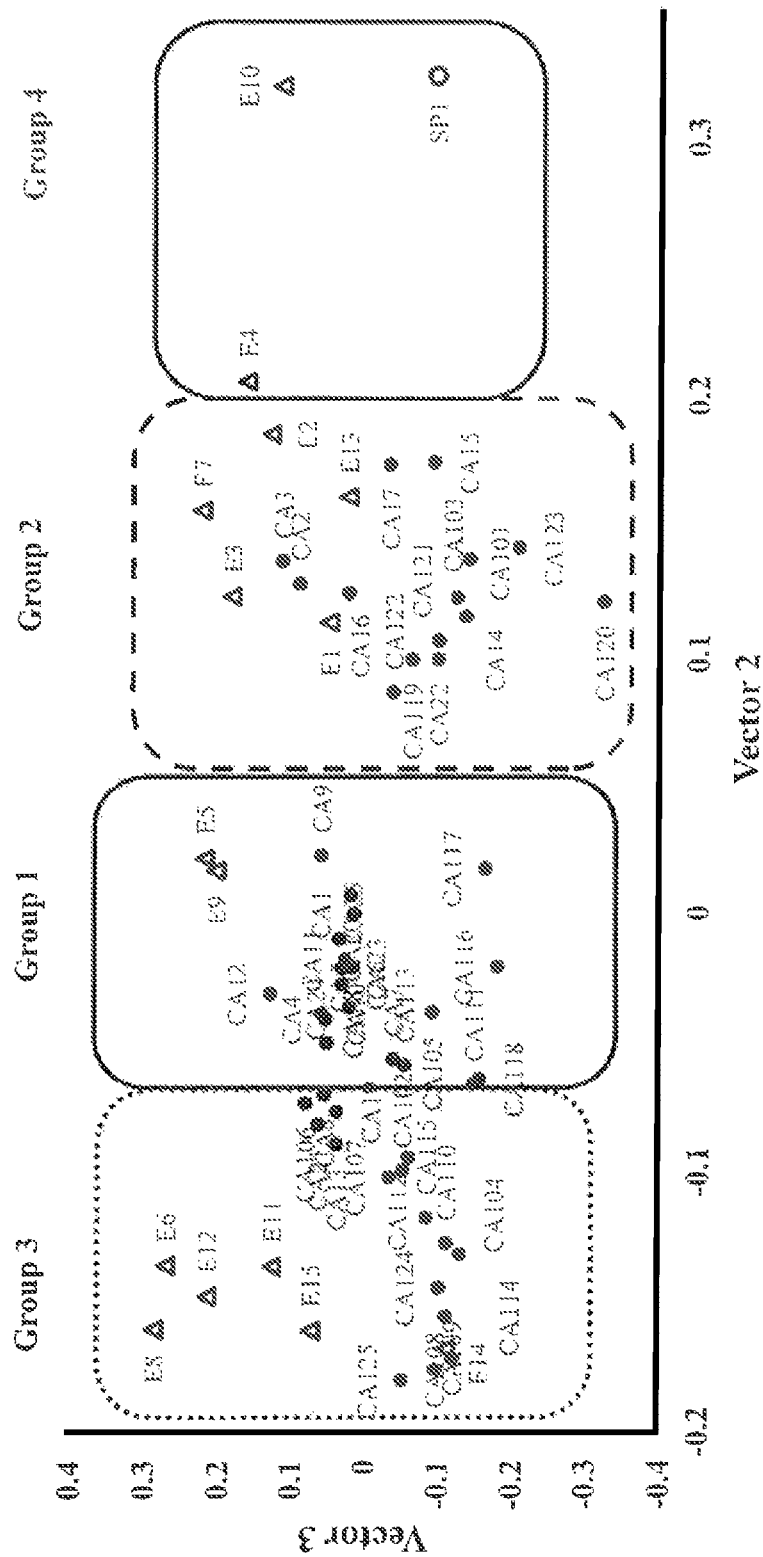

The only EVOOs that did not relate to any of Groups 1, 2 or 3 were three oils having a low content of 18:2n-6 ranging from 1.5% to 4%. A fourth grouping (Group 4), as shown in FIG. 6D was developed, and a fourth set of PLS1 calibration models was prepared for this group.

It is of interest to note that the content of 18:2n-6 in these olive oils appeared to play a pivotal role in the identification of EVOO varieties and in the development of the blend-specific or variety-specific PLS1 calibration models. Specifically, for all EVOOs investigated, the ranges of 18:2 n-6 were, as stated above, each within a specific and fairly narrow range, namely: between 9.5% and 12.7% for Group 1, between 5.0% and 9.9% for Group 2, between 10.7% and 14.8% for Group 3, and from 1.5 to 4% for Group 4. Thus, it was determined that the level of 18:2n-6 present in the EVOO could be used as a first pre-selection classification method, and the Group classifications and PLS1 calibration models could be prepared around this pre-selection classification scheme.

Using this approach, or more preferably, using a pre-selection approach such as the IDENT system, the EVOO samples could now be pre-classified into one of the four different Groups, in accordance with this example.

Once we established the existence of four groups (FIG. 6D) all of the samples were analyzed using the respective PLS1 calibration models for their particular group, in order to determine their LA, OA, PO, and RO contents. The samples were also analyzed for their FT-NIR Index and FA composition.

The results from the EVOO's tested in this example are shown in Tables 2 to 5, wherein Group 1 oils of acceptable quality are shown in Table 2A, while EVOOs oils suspected of being adulterated, are shown in Table 2B. Similar tables for oils in Group 2 are shown in Tables 3A and 3B respectively, and similar tables for oils in Group 3 are shown in Tables 4A and 4B respectively. Finally, the results for the oils in Group 4 are shown in Tables 5A and 5B. In each of Tables 2 to 5, the FT-NIR Index is shown, as well as the predicted level of selected FA's, and predicted levels of adulterants using the appropriate PLS1 calibration models for that group. In the tables showing the suspected adulterated oils, the FT-NIR Index is shown in bold if below the preferred minimum index value of 75. Further, if the predicted level of LA, OA, PO or RO is higher than the expected values for that classification group, the sample has been shown in bold. This is evidence that the sample may have been adulterated with an oil, such as refined olive oil, corn oil, or hazelnut oil, is suspected.

Accordingly, the present invention also provides a method for determining in an edible oil sample comprising:

determining an FT-NIR Index for the sample to be tested, and determining that said FT-NIR Index value is above an accepted value;

determining the fatty acid (FA) composition for the sample to be tested, and confirming that FA levels are within EVOO standards; and determining the predicted levels in said sample of adulterant oils high in linoleic acid (LA), oleic acid (OA), palmitic acid (PO), or refined olive oil (RO), using the calibration models for the selected classification, in order to determine that these levels are within accepted levels for the edible oil being analysed.

As noted, if the correct set of PLS1 calibration models were used, all the predictions for LA and PO were low, as expected. On the other hand, the predictions for OA concentrations in these products were slightly higher than expected.

The predicted RO content of all EVOO samples using the appropriate set of one of the four PLS1 calibration models generally showed a greater variation than those found for the predicted values for LA, OA or PO. This is attributed to extensive handling or age of many of the EVOO samples which reduces the content of volatiles and results in a lower FT-NIR Index value and a higher RO value. It was evident from these results that the RO values for some samples was higher than for others, and this might be related to the fact that some samples were older than others, or taken from non-original sources. However, it should be noted that higher predicted RO values can also be due to intentional adulteration of the EVOO with a refined olive oil, and the present technique has difficulty in differentiating between low levels of aging of the EVOO, and slight adulteration with a refined oil.

While the RO content of EVOOs seldom exceeds a value of 20, with a few exceptions, intentional adulteration of an EVOO with a refined olive oil is clearly identifiable at more than 20% using the respective PLS1 calibration models and a significant decrease in the FT-NIR Index. The few exceptions noticed are probably handling issue rather than adulteration. In either case, the loss of volatiles from an EVOO leads to a lower quality olive oil which is associated with a lower FT-NIR Index value, a rise in RO content, or as concluded in various studies, a loss in the EVOO status. It has been suggested that the most common and least detected adulterations of olive oil are of those oils that have been processed at low heat to remove odors and tastes. Unfortunately, this type of adulteration or the loss of volatiles is also difficult to differentiate with FT-NIR at less than 20%. However, from a regulatory point of view, a significant level of RO in EVOO, regardless of whether it is the results of unintentional mishandling or intentional deodorization leading to loss of volatiles detected by a lower FT-NIR Index value or a rise in RO content due to adulteration, should be deemed sufficient to flag and disqualify such a product from the "extra virgin" status.

It should also be noted that the 18:2 n-6 content alone might not be the only factor used to determine the group classification of a specific variety of EVOO. For this analysis, the consistency of the results obtained with all the other PLS1 calibration models developed to determine the FT-NIR Index, the FA composition, and for the prediction of type and amount of adulteration, might also be used. Also, additional Groups may be required for oils falling outside of the tested ranges. For example, EVOOs with an 18:2 n-6 content exceeding 15% have been reported in the IOC standards, but these oils were not tested, and it is not known if an additional classification group is required for these oils.

Using the PLS1 calibration models prepared for Groups 1 to 4, a variety of EVOOs were also tested wherein two different single varieties of oils were blended to see if blending varieties would result in different grouping. To test the effect of blending, two single varieties of oils were selected with extreme differences in their 18:2n-6 content, namely E10 (Table 5A, Sample No. 2) which was an oil of the Picual variety with an 18:2n-6 content of 1.5%, and E14 (Table 4A, Sample No. 2) of the Arbequina variety with an 18:2n-6 content of 14.6%. These oils were from Groups 4 and 3, respectively.

Figure 7:
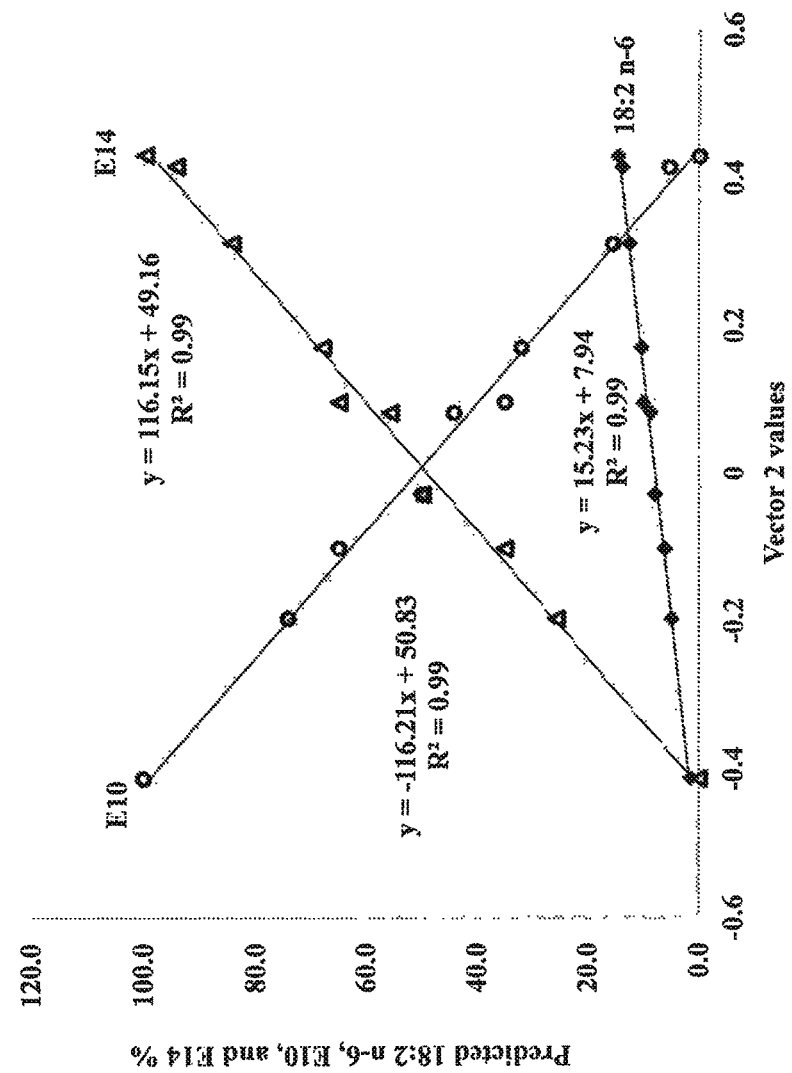
FIGS. 7 and 8 show results for a blend of two oils, from 2 different IDENT groups.

Samples were prepared and tested for blends from 100% Picual mixed with incremental addition of Arbequina up to 65%, and for the reverse addition of from 100% Arbequina mixed with incremental addition of Picual up to 74.3%. The results were analyzed and subsequently plotting the 18:2 n-6 content of the blend as well as the content of each of the two varieties in the blended samples vs. Vector 2 (FIG. 7). As can be observed, all three functions showed good correlation.

Moreover, when the individual mixtures were analyzed for determining group membership in one of the four groups, it was noted that group membership was dependent on the content of 18:2n-6 in the mixtures. This simple demonstration shows that by blending single varieties with each other one can prepare any blend with new selective chemical characteristics.

Figure 8:
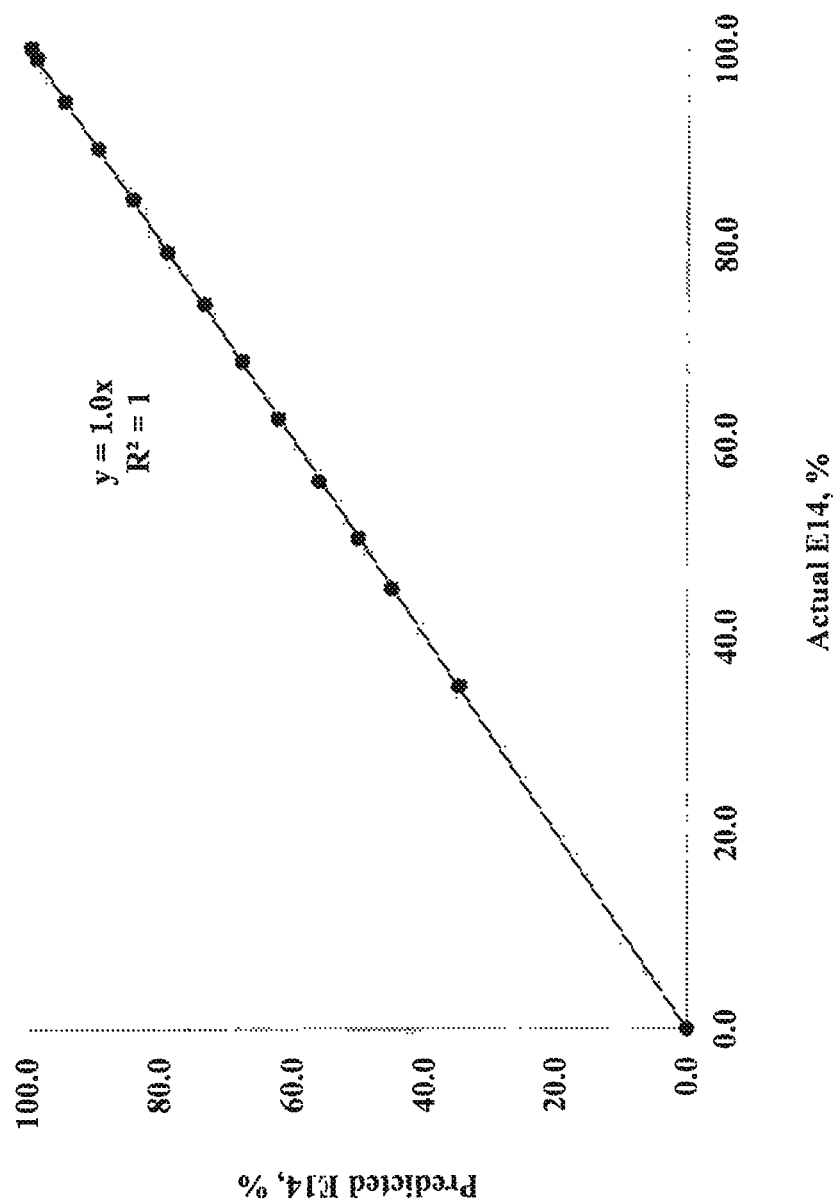

Further, these blends were used to develop a simple two component quantitative PLS1 calibration model and this could be used to accurately predict the concentration of each variety, Picual (E10) or Arbequina (E14) in the blend (FIG. 8). This experiment shows that any blend can be generated by preparing accurate concentrations of single varieties, and have their respective concentrations predicted by using a PLS1 calibration model. In addition, this blending study may provide an explanation of why the scores of most of the EVOO samples appear to cluster near the middle of FIG. 3. This may be because blends represent the average matrix of individual varieties and might obscure or dilute the unique characteristics of some varieties with very different FA profiles.

It has also been noted that the FT-NIR Index value can be a major marker for quality or purity since it exhibits a high correlation between the EVOOs' content of volatile carbonyl type components and the observed overtone absorption in the FT-NIR spectra near 5269 $cm^{-1}$. The FT-NIR Index values are a major contributing factor to vector 3 in FIG. 5, However, it appears that differences in this factor (FT-NIR Index) were less discriminatory with respect to group membership than the different concentrations of 18:2n-6, and hence there not be any need to modify the PLS1 calibration models with respect to the FT-NIR Index.

It should also be again emphasized that in the present example, the tested EVOO oils were grouped into four Groups or classifications (named Group 1, 2, 3, and 4). While any number of Groups can be developed, the selection of four Groups seemed to adequately cover the range of EVOO oils to be tested in this example. Then, a total of four different calibration models for each of the four different groups were determined by FT-NIR and PLS1, in order to better represent all the EVOO products analyzed. This group classification was therefore of assistance in order to properly select the best set of classification models for that oil, and thereby address some of the challenges presented by products having different blends, or by having single varieties of EVOOs from various sources.

Figure 9:
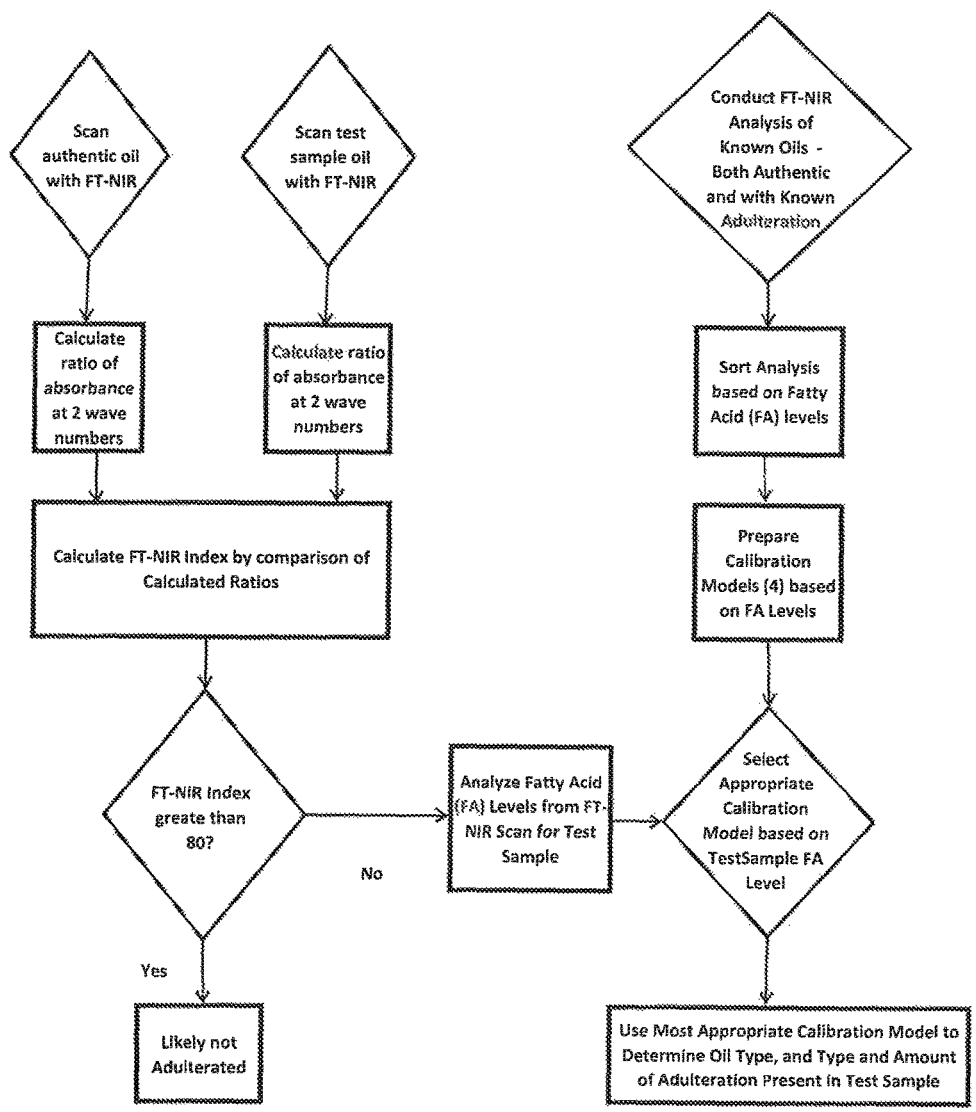
FIG. 9 shows a flow chart of the overall method of the present embodiment.

As such, a preferred method of the present embodiment is one in which FT-NIR spectroscopy analysis comprises determining an FT-NIR Index for the sample to be tested, and determining that said FT-NIR Index value is above an accepted value; determining the fatty acid (FA) composition for the sample to be tested, and confirming that FA levels are within the EVOO standards; and then determining the predicted levels of adulterant oils high in linoleic acid (LA), such as corn oil, oleic acid (OA), such as hazelnut oil, palmitic acid (PO), such as palm olein, or refined olive oil (RO), using the calibration models for the selected classification, to determine that these levels are within accepted levels for the edible oil being analysed. A summary of this process is shown in FIG. 9 in which the process steps are identified for a system having four classification models, and a preferred FT-NIR Index level of 80%.

Determining the Type and Amount of Adulterant in an EVOO

To establish with greater certainty which adulterant was mixed with EVOO, and by how much, required the development of independent PLS1 calibration models based on gravimetrically prepared mixtures of authentic EVOO and adulterants. It was concluded that it was unlikely that a single FT-NIR model could be easily prepared that would determine the presence of different edible oils in EVOO.

The characteristic feature of an authentic EVOO is a high FT-NIR Index, a FA composition within the expected ranges for olive oils, and low predicted values for potential adulterant calibration models (i.e LA, OA, PO and RO limits, as shown, for example, in Tables 2 to 5).

Thus, it is apparent that there has been provided, in accordance with the present invention, an analytical technique for the testing of an edible oil, and an EVOO in particular, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps. Further, the invention illustratively disclosed herein suitably may be practised in the absence of any element which is not specifically disclosed herein. Also, unless otherwise specifically noted, all of the features described herein may be combined with any of the above aspects, in any combination.

Moreover, words such as "substantially" or "essentially", when used with an adjective or adverb is intended to enhance the scope of the particular characteristic; e.g., substantially planar is intended to mean planar, nearly planar and/or exhibiting characteristics associated with a planar element.

Further, use of the terms "he", "him", or "his", is not intended to be specifically directed to persons of the masculine gender, and could easily be read as "she", "her", or "hers", respectively.

Also, while this discussion has addressed prior art known to the inventor, it is not an admission that all art discussed is citable against the present application.

TABLE 1

Typical FA concentrations (as % of total FA) of selected plant oils analyzed by GC

|  | 16:0 | 18:0 | 18:1n-9 | 18:2n-6 | 18:3n-3 |
|---|---|---|---|---|---|
| Extra virgin olive oil | 11.8 | 2.9 | 69.6 | 10.1 | 0.7 |
| Soybean oil | 10.1 | 4.6 | 24.2 | 50.2 | 6.8 |
| Sunflower oil | 6.6 | 3.4 | 28.0 | 59.3 | 0.1 |
| Corn oil | 11.6 | 2.0 | 28.5 | 54.2 | 1.4 |
| Canola oil | 4.1 | 1.8 | 59.9 | 19.4 | 6.9 |
| Hazelnut oil | 6.3 | 2.8 | 76.2 | 12.1 | 0.2 |
| High oleic acid safflower oil | 5.4 | 1.9 | 73.8 | 16.2 | 0.2 |
| Peanut oil | 10.2 | 2.8 | 53.7 | 25.5 | 0.1 |
| Palm olein | 37.3 | 4.1 | 43.0 | 11.7 | 0.2 |
| Refined olive oil | 12.8 | 3.1 | 70.2 | 8.3 | 0.7 |

TABLE 2A

Group 1 FT-NIR analysis of EVOO samples for quality and purity

| | | | Predicted % FA (% of total FA) | | | | | Predicted % adulterant in EVOO | | | |
|---|---|---|---|---|---|---|---|---|---|---|---|
| | IDENT Library | FT-NIR | 16:0 | 18:0 | 18:1n-9 | 18:2n-6 | 18:3n-3 | Model 1 (LA) | Model 2 (OA) | Model 3 (PO) | Model 4 (RO) |
| | | | Standard IOC Range, % | | | | | Mean ± 2SD for reference EVOO | | | |
| Sample No. | Group | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 1 | 120.6 | 13.5 | 1.8 | 68.8 | 7.4 | 1.2 | −1.3 | −0.9 | −4.9 | −15.6 |
| 2 | 1 | 104.0 | 13.43 | 2.6 | 69.4 | 10.4 | 1.2 | 1.3 | 9.6 | −6.6 | −4.4 |
| 3 | 1 | 103.9 | 14.71 | 3.2 | 64.3 | 11.7 | 0.3 | 2.0 | 9.9 | −6.3 | −1.7 |
| 4 | 1 | 102.4 | 13.13 | 2.7 | 63.7 | 10.5 | 0.8 | 1.1 | 6.2 | −4.2 | 0.6 |
| 5 | 1 | 102.0 | 14.23 | 3.0 | 63.7 | 11.9 | 0.4 | 1.0 | 9.3 | −5.0 | −2.3 |
| 6 | 1 | 101.5 | 14.2 | 3.3 | 65.9 | 10.4 | 0.9 | 0.7 | 9.0 | −3.3 | −22.9 |
| 7 | 1 | 100.0 | 15.61 | 3.2 | 61.5 | 11.2 | −0.2 | −0.7 | 0.9 | 0.0 | −1.7 |
| 8 | 1 | 99.7 | 14.9 | 2.4 | 66.6 | 11.2 | 0.2 | 1.8 | 9.3 | −4.6 | 0.3 |
| 9 | 1 | 99.6 | 14.2 | 2.4 | 64.6 | 11.4 | 0.2 | 2.0 | 10.2 | −3.6 | −16.3 |
| 10 | 1 | 99.4 | 15.37 | 2.9 | 63.6 | 11.6 | 0.9 | 1.9 | 5.2 | −2.8 | −1.7 |
| 11 | 1 | 98.5 | 14.76 | 2.7 | 66.8 | 11.7 | 0.6 | 1.6 | 10.2 | −4.8 | −15.7 |
| 12 | 1 | 97.7 | 14.55 | 3.1 | 66.7 | 11.5 | 0.4 | 0.6 | 6.3 | −0.8 | −1.5 |
| 13 | 1 | 97.5 | 15.31 | 2.8 | 66.3 | 11.1 | 0.8 | 1.5 | 3.3 | −1.5 | −6.7 |
| 14 | 1 | 96.3 | 15.26 | 2.8 | 63.4 | 11.5 | 0.5 | 0.2 | 2.2 | −2.6 | 0.2 |
| 15 | 1 | 96.1 | 14.48 | 2.7 | 67.5 | 10.6 | 0.8 | 0.0 | 4.4 | −2.6 | −2.0 |
| 16 | 1 | 95.6 | 14.22 | 2.6 | 69.6 | 11.1 | 0.6 | 2.0 | 12.3 | −4.6 | −6.5 |
| 17 | 1 | 94.4 | 15.24 | 3.1 | 64.3 | 11.5 | 0.3 | 1.8 | 5.1 | −0.3 | −15.2 |
| 18 | 1 | 94.2 | 13.52 | 3.1 | 64.7 | 12.7 | 0.2 | 2.2 | 11.5 | −4.3 | −4.9 |
| 19 | 1 | 93.3 | 15.3 | 2.6 | 69.9 | 10.0 | 0.4 | −0.2 | 3.6 | −1.2 | 5.7 |
| 20 | 1 | 92.2 | 13.5 | 3.1 | 67.2 | 11.3 | 0.9 | 3.0 | 13.4 | −5.2 | 2.5 |
| 21 | 1 | 91.7 | 12.5 | 1.4 | 69.9 | 9.4 | 0.3 | 0.1 | 9.6 | −4.5 | −3.2 |
| 22 | 1 | 91.6 | 15.22 | 2.5 | 69.4 | 9.8 | 1.3 | 0.0 | 3.9 | −0.8 | 6.7 |
| 23 | 1 | 89.3 | 13.9 | 2.4 | 64.7 | 6.7 | 0.9 | 0.2 | 5.4 | −1.7 | −5.5 |
| 24 | 1 | 87.1 | 14.7 | 3.0 | 66.6 | 11.0 | 0.4 | 0.8 | 6.2 | −0.6 | 4.1 |
| 25 | 1 | 86.3 | 12.6 | 2.3 | 67.9 | 7.8 | 1.2 | 1.1 | 11.3 | −2.4 | 2.6 |
| 26 | 1 | 84.4 | 15.1 | 3.2 | 67.2 | 11.0 | 0.2 | 0.7 | 8.4 | −1.1 | 6.1 |
| 27 | 1 | 84.3 | 13.6 | 2.1 | 70.8 | 9.0 | 0.4 | 2.2 | 12.2 | −5.0 | 0.4 |
| 28 | 1 | 83.4 | 13.1 | 2.7 | 66.6 | 7.4 | 1.0 | 3.0 | 13.7 | −5.8 | 13.6 |
| 29 | 1 | 80.3 | 13.5 | 2.3 | 67.3 | 10.4 | 0.1 | 1.0 | 7.5 | −1.1 | −20.3 |
| 30 | 1 | 80.2 | 15.0 | 2.5 | 68.8 | 8.7 | 1.4 | 2.5 | 10.7 | −2.9 | −6.5 |
| 31 | 1 | 80.2 | 14.7 | 2.2 | 68.6 | 9.3 | 0.7 | 2.1 | 8.7 | −3.3 | 18.9 |
| 32 | 1 | 75.8 | 12.9 | 2.8 | 69.8 | 8.0 | 0.9 | 1.2 | 6.2 | −2.9 | 6.6 |
| 33 | 1 | 75.1 | 13.3 | 2.2 | 68.6 | 9.5 | 0.5 | 1.5 | 9.3 | −3.0 | 10.5 |

TABLE 2B

Group 1 FT-NIR analysis of EVOO samples with potential adulteration

| | | | Predicted % FA (% of total FA) | | | | | Predicted % adulterant in EVOO | | | |
|---|---|---|---|---|---|---|---|---|---|---|---|
| | IDENT Library | FT-NIR | 16:0 | 18:0 | 18:1n-9 | 18:2n-6 | 18:3n-3 | Model 1 (LA) | Model 2 (OA) | Model 3 (PO) | Model 4 (RO) |
| | | | | | Standard IOC Range, % | | | | Mean ± 2SD for reference EVOO | | |
| Sample No. | Group | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 1 | 96.2 | 14.9 | 3.1 | 64.5 | 12.3 | 0.9 | 3.3 | 8.3 | −4.2 | 3.5 |
| 2 | 1 | 95.6 | 12.8 | 1.8 | 71.4 | 6.7 | 1.2 | 2.4 | 15.4 | −12.1 | −12.4 |
| 3 | 1 | 91.8 | 13.5 | 2.0 | 72.1 | 9.4 | 0.4 | 2.6 | 16.7 | −7.8 | −7.8 |
| 4 | 1 | 85.4 | 13.2 | 2.0 | 67.8 | 8.3 | 0.6 | 4.0 | 20.2 | −10.2 | 0.9 |
| 5 | 1 | 81.3 | 13.6 | 1.7 | 69.7 | 6.9 | 0.4 | 1.4 | 12.9 | −4.9 | 21.3 |
| 6 | 1 | 80.6 | 14.3 | 2.8 | 68.3 | 10.3 | 0.2 | 2.3 | 11.6 | −6.6 | 21.5 |
| 7 | 1 | 80.4 | 11.5 | 1.7 | 72.7 | 7.2 | 0.8 | 0.9 | 17.1 | −7.4 | 14.1 |
| 8 | 1 | 80.0 | 12.4 | 2.9 | 69.7 | 9.5 | 0.7 | 3.3 | 20.0 | −6.4 | 34.8 |
| 9 | 1 | 79.8 | 14.2 | 2.2 | 67.8 | 8.4 | 1.5 | 5.2 | 22.9 | −7.2 | 17.6 |
| 10 | 1 | 79.3 | 13.6 | 2.6 | 69.8 | 9.0 | 1.2 | 3.8 | 19.9 | −8.3 | 23.4 |
| 11 | 1 | 78.8 | 13.7 | 2.5 | 64.6 | 11.0 | 0.0 | 3.3 | 14.3 | −5.7 | 16.3 |
| 12 | 1 | 78.7 | 12.6 | 2.3 | 63.8 | 10.2 | 0.9 | 3.7 | 17.9 | −3.8 | 3.1 |
| 13 | 1 | 78.6 | 12.4 | 1.7 | 69.8 | 8.2 | 0.3 | 3.1 | 19.4 | −8.9 | 4.2 |
| 14 | 1 | 76.7 | 13.0 | 2.2 | 68.5 | 8.4 | −0.1 | 1.9 | 16.1 | −5.0 | 33.7 |
| 15 | 1 | 76.2 | 14.3 | 1.7 | 66.5 | 10.2 | 0.9 | 3.2 | 17.1 | −5.7 | 20.2 |
| 16 | 1 | 76.1 | 13.6 | 1.9 | 69.3 | 8.8 | 0.9 | 2.8 | 16.9 | −5.6 | 35.8 |
| 17 | 1 | 75.2 | 12.4 | 2.0 | 69.0 | 7.1 | 0.9 | 2.5 | 21.3 | −6.8 | 24.2 |
| 18 | 1 | 75.0 | 12.0 | 2.0 | 71.3 | 8.7 | 1.4 | 2.8 | 17.2 | −6.6 | 19.8 |
| 19 | 1 | 74.9 | 9.4 | 2.2 | 72.9 | 7.8 | 0.4 | 3.1 | 28.9 | −13.2 | 18.6 |
| 20 | 1 | 73.8 | 14.6 | 2.9 | 64.9 | 11.1 | 0.8 | 4.6 | 16.6 | −3.4 | 23.4 |
| 21 | 1 | 72.7 | 12.7 | 2.1 | 72.7 | 5.5 | 1.5 | 1.9 | 16.5 | −5.8 | 45.2 |
| 22 | 1 | 72.2 | 11.9 | 1.9 | 73.0 | 9.3 | 0.8 | 3.1 | 21.9 | −9.1 | 22.9 |
| 23 | 1 | 71.7 | 12.3 | 2.0 | 76.4 | 7.5 | 0.6 | 2.5 | 18.4 | −9.4 | 35.3 |
| 24 | 1 | 71.6 | 14.4 | 2.4 | 67.2 | 11.0 | −0.4 | 0.9 | 8.0 | −2.9 | 17.7 |
| 25 | 1 | 71.5 | 15.1 | 2.6 | 64.2 | 10.7 | −0.1 | 1.9 | 13.0 | −2.1 | 19.5 |
| 26 | 1 | 70.6 | 13.6 | 2.3 | 66.3 | 9.6 | 0.6 | 4.7 | 22.3 | −5.8 | 19.5 |
| 27 | 1 | 69.6 | 14.7 | 2.8 | 67.1 | 11.2 | −0.3 | 1.7 | 11.5 | −2.4 | 10.1 |
| 28 | 1 | 69.4 | 12.9 | 2.2 | 71.5 | 8.4 | −0.1 | 1.6 | 19.2 | −5.5 | 37.6 |
| 29 | 1 | 69.4 | 13.8 | 2.3 | 69.7 | 10.3 | 0.1 | 3.8 | 19.0 | −4.9 | 25.3 |
| 30 | 1 | 69.1 | 12.5 | 2.7 | 71.4 | 7.1 | 1.5 | 2.3 | 14.8 | −3.9 | 24.7 |
| 31 | 1 | 69.0 | 14.3 | 2.4 | 66.4 | 10.4 | −0.7 | 1.0 | 11.1 | −2.3 | 22.2 |
| 32 | 1 | 69.0 | 14.6 | 2.8 | 67.9 | 9.3 | 0.5 | 3.2 | 14.0 | −2.9 | 10.6 |
| 33 | 1 | 68.1 | 13.4 | 2.5 | 71.1 | 8.0 | 0.6 | 1.6 | 10.5 | −3.3 | 19.4 |
| 34 | 1 | 67.7 | 14.7 | 2.5 | 66.0 | 9.2 | 0.3 | 5.6 | 21.7 | −6.5 | −4.1 |
| 35 | 1 | 67.5 | 15.2 | 2.9 | 67.9 | 8.4 | 1.6 | 3.5 | 14.3 | −1.9 | 35.5 |
| 36 | 1 | 66.1 | 12.1 | 2.2 | 69.9 | 9.0 | −0.1 | 3.2 | 24.0 | −7.6 | 31.1 |
| 37 | 1 | 64.6 | 13.7 | 2.1 | 71.4 | 5.5 | 2.0 | 1.6 | 12.6 | −1.0 | 54.2 |
| 38 | 1 | 62.5 | 14.7 | 2.1 | 70.1 | 7.9 | 1.1 | 4.3 | 14.5 | −3.3 | 38.9 |
| 39 | 1 | 60.0 | 12.9 | 2.4 | 75.8 | 7.9 | 1.2 | 3.4 | 16.7 | −3.3 | 39.0 |
| 40 | 1 | 59.9 | 13.2 | 1.9 | 71.8 | 8.3 | 1.6 | 4.3 | 18.6 | −6.1 | 40.3 |
| 41 | 1 | 58.7 | 12.1 | 2.9 | 70.6 | 8.1 | 0.6 | 2.4 | 21.8 | −4.7 | 39.5 |
| 42 | 1 | 57.8 | 13.9 | 2.8 | 62.6 | 11.3 | 0.5 | 5.5 | 20.0 | −1.6 | 30.4 |
| 43 | 1 | 57.4 | 14.7 | 3.1 | 70.6 | 9.0 | −0.3 | 3.1 | 14.7 | −3.6 | 35.7 |
| 44 | 1 | 57.3 | 16.2 | 3.0 | 64.7 | 11.3 | 0.5 | 5.3 | 20.4 | −4.6 | 55.9 |
| 45 | 1 | 57.1 | 12.1 | 1.9 | 69.0 | 7.5 | 0.6 | 2.1 | 13.6 | −1.7 | 58.2 |
| 46 | 1 | 46.0 | 14.7 | 3.0 | 65.4 | 10.0 | 1.2 | 6.3 | 23.6 | −2.0 | 44.2 |
| 47 | 1 | 45.8 | 13.4 | 1.9 | 69.0 | 7.3 | 0.8 | 2.6 | 15.2 | −0.4 | 37.0 |
| 48 | 1 | 15.0 | 13.7 | 2.4 | 67.8 | 10.0 | 0.0 | 5.5 | 24.5 | 0.5 | 98.1 |

TABLE 3A

Group 2 FT-NIR analysis of EVOO samples for quality and purity

| | | | Predicted % FA (% of total FA) | | | | | Predicted % adulterant in EVOO | | | |
|---|---|---|---|---|---|---|---|---|---|---|---|
| | IDENT Library | FT-NIR | 16:0 | 18:0 | 18:1n-9 | 18:2n-6 | 18:3n-3 | Model 1 (LA) | Model 2 (OA) | Model 3 (PO) | Model 4 (RO) |
| | | | | | Standard IOC Range, % | | | | Mean ± 2SD for reference EVOO | | |
| Sample No. | | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 2 | 117.8 | 14.41 | 3.6 | 64.8 | 9.3 | 0.5 | −1.1 | −3.6 | 3.7 | −19.7 |
| 2 | 2 | 106.0 | 15.37 | 2.7 | 68.5 | 9.4 | 0.2 | 0.2 | 4.5 | −1.5 | 1.6 |
| 3 | 2 | 104.7 | 13.5 | 2.3 | 72.5 | 6.1 | 0.4 | −2.2 | −1.0 | −4.5 | −17.3 |
| 4 | 2 | 104.5 | 13.28 | 2.7 | 73.5 | 6.7 | 0.7 | 0.0 | 3.1 | −2.5 | −1.6 |
| 5 | 2 | 103.8 | 12.69 | 2.5 | 75.0 | 6.8 | 1.0 | 0.4 | 4.8 | −6.9 | −10.7 |
| 6 | 2 | 103.5 | 15.33 | 3.2 | 67.6 | 9.2 | −0.2 | −2.2 | −3.1 | 2.5 | −3.6 |
| 7 | 2 | 99.8 | 13.8 | 2.6 | 71.5 | 7.7 | 0.5 | 1.6 | 0.5 | −0.5 | −0.2 |

TABLE 3A-continued

Group 2 FT-NIR analysis of EVOO samples for quality and purity

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 8 | 2 | 99.2 | 14.13 | 2.9 | 76.1 | 6.8 | 1.1 | −0.8 | −0.9 | −1.3 | −24.6 |
| 9 | 2 | 95.7 | 14.22 | 3.3 | 69.7 | 7.8 | 0.4 | −1.4 | −1.1 | −1.3 | 12.3 |
| 10 | 2 | 94.2 | 14.91 | 2.8 | 68.2 | 9.9 | −0.3 | 1.1 | 6.5 | 1.5 | 13.5 |
| 11 | 2 | 94.2 | 15.53 | 2.8 | 66.3 | 8.9 | 0.8 | 1.1 | 3.8 | 6.0 | 1.2 |
| 12 | 2 | 93.8 | 15.13 | 2.9 | 71.3 | 7.5 | 0.3 | −2.8 | −1.4 | 1.5 | −22.7 |
| 13 | 2 | 90.4 | 12.16 | 2.1 | 73.2 | 7.3 | 0.8 | 1.3 | 6.2 | −4.1 | 1.8 |
| 14 | 2 | 89.7 | 13.61 | 2.2 | 72.4 | 6.8 | 0.6 | 0.6 | 3.6 | −6.8 | 5.3 |
| 15 | 2 | 88.2 | 12.5 | 1.9 | 73.9 | 5.2 | 0.2 | −1.1 | −2.4 | −5.2 | −21.9 |
| 16 | 2 | 87.5 | 12.2 | 2.1 | 74.9 | 4.2 | 1.4 | 1.5 | 7.8 | −5.5 | 4.9 |
| 17 | 2 | 86.8 | 12.3 | 2.0 | 73.1 | 7.7 | 0.3 | 2.3 | 10.4 | −7.0 | 6.0 |
| 18 | 2 | 86.7 | 13.3 | 2.5 | 72.2 | 6.4 | 0.2 | −0.7 | −2.8 | 1.7 | −8.9 |
| 19 | 2 | 86.2 | 13.8 | 2.9 | 69.4 | 5.5 | 1.0 | 1.1 | 7.8 | 4.7 | 17.5 |
| 20 | 2 | 84.6 | 14.86 | 2.3 | 72.9 | 7.7 | 1.5 | 0.3 | 3.5 | 2.3 | 2.8 |
| 21 | 2 | 83.9 | 13.8 | 2.5 | 75.9 | 4.8 | 0.6 | 0.1 | 2.3 | −3.6 | −2.4 |
| 22 | 2 | 82.4 | 12.9 | 1.9 | 76.9 | 5.9 | 0.1 | 1.0 | 3.6 | −4.3 | 0.0 |
| 23 | 2 | 81.8 | 13.4 | 2.4 | 73.3 | 8.0 | 0.0 | 0.9 | 8.7 | −0.9 | 15.5 |
| 24 | 2 | 80.4 | 13.9 | 2.0 | 72.2 | 6.4 | 0.7 | 0.3 | 2.4 | −0.5 | 9.6 |
| 25 | 2 | 79.7 | 12.5 | 2.3 | 72.4 | 6.4 | 1.0 | 2.3 | 9.7 | −2.7 | 5.7 |
| 26 | 2 | 78.7 | 13.3 | 2.8 | 73.2 | 3.4 | 1.0 | −0.7 | −0.3 | −4.5 | −4.1 |

TABLE 3B

Group 2 FT-NIR analysis of EVOO samples with potential adulteration

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 2 | 88.6 | 14.2 | 3.3 | 70.6 | 8.2 | 0 | 1.5 | 8.1 | 0.8 | *24.0* |
| 2 | 2 | 81.1 | 14.4 | 2.5 | 72.4 | 6.7 | 0.2 | 1.8 | 6.8 | −6.3 | *25.4* |
| 3 | 2 | 80.2 | 14.3 | 2.0 | 68.8 | 8.6 | 0.3 | 1.3 | 10.2 | −2.0 | *40.6* |
| 4 | 2 | 80.1 | 13.2 | 1.9 | 78.9 | 4.3 | 1.7 | 1.0 | 9.3 | −5.3 | *26.7* |
| 5 | 2 | 79.7 | 12.2 | 1.9 | 72.1 | 6.9 | 0.3 | 1.4 | 8.4 | *−10.7* | 11.4 |
| 6 | 2 | 79.6 | 13.7 | 2.1 | 70.2 | 7.6 | −0.1 | *3.1* | 19.0 | −7.1 | *33.1* |
| 7 | 2 | 79.0 | 12.6 | 1.9 | 72.9 | 5.0 | 0.7 | 0.8 | 7.7 | *−8.1* | 8.5 |
| 8 | 2 | 77.9 | 14.1 | 2.6 | 73.3 | 6.7 | 1.0 | *3.1* | 14.5 | −3.3 | *35.5* |
| 9 | 2 | 77.8 | 11.7 | 2.3 | 71.0 | 6.4 | 1.1 | 2.6 | *17.1* | −6.9 | *24.8* |
| 10 | 2 | 77.8 | 12.4 | 2.3 | 71.8 | 6.9 | 1.3 | *3.6* | *22.5* | *−8.0* | *52.1* |
| 11 | 2 | 77.6 | 13.2 | 2.3 | 73.1 | 7.2 | 1.0 | *4.8* | *20.3* | −2.9 | *48.8* |
| 12 | 2 | 77.1 | 12.9 | 2.0 | 70.8 | 8.2 | 0.3 | 1.3 | 7.8 | *−9.0* | *41.6* |
| 13 | 2 | 77.0 | 12.6 | 1.8 | 70.2 | 6.5 | 0.3 | 1.2 | 9.3 | −5.1 | *21.3* |
| 14 | 2 | 76.5 | 10.9 | 2.0 | 73.2 | 6.1 | 0.8 | 2.9 | 14.9 | *−12.1* | *44.0* |
| 15 | 2 | 76.4 | 14.4 | 2.2 | 70.6 | 7.3 | 0.4 | 0.1 | 4.9 | 2.1 | *23.6* |
| 16 | 2 | *74.2* | 13.5 | 2.0 | 70.5 | 8.4 | 0.4 | 2.8 | 14.4 | −2.3 | *45.4* |
| 17 | 2 | *74.2* | 11.8 | 2.2 | 71.6 | 7.6 | 0.7 | 2.2 | 14.2 | −5.3 | *38.8* |
| 18 | 2 | *73.8* | 12.0 | 2.4 | 75.0 | 5.5 | 0.6 | *3.1* | 16.2 | *−9.2* | *38.4* |
| 19 | 2 | *73.2* | 13.3 | 2.7 | 65.5 | 7.4 | −0.6 | 1.4 | 6.7 | −1.0 | *23.8* |
| 20 | 2 | *72.7* | 12.8 | 1.8 | 71.1 | 6.9 | 0.7 | 2.5 | 13.5 | −5.6 | *27.8* |
| 21 | 2 | *72.6* | 13.0 | 1.7 | 72.6 | 8.3 | 0.6 | *4.2* | 13.8 | −4.5 | *51.3* |
| 22 | 2 | *70.7* | 12.4 | 2.1 | 71.3 | 8.4 | 0.2 | *3.7* | *17.6* | *−10.5* | *41.2* |
| 23 | 2 | *70.6* | 11.3 | 1.5 | 72.9 | 6.1 | 0.7 | *3.8* | *16.5* | *−10.0* | *24.9* |
| 24 | 2 | *70.4* | 12.4 | 2.4 | 70.3 | 7.5 | 0.0 | 2.3 | 14.3 | −4.0 | *24.8* |
| 25 | 2 | *68.4* | 13.8 | 2.6 | 75.6 | 6.8 | −0.2 | 2.1 | 9.1 | *−10.4* | *27.2* |
| 26 | 2 | *68.3* | 11.9 | 2.4 | 73.3 | 6.5 | 1.0 | 2.7 | *15.2* | *−8.4* | *33.0* |
| 27 | 2 | *68.3* | 12.4 | 2.9 | 72.8 | 5.9 | 0.2 | 0.8 | 9.1 | −3.2 | *26.2* |
| 28 | 2 | *67.7* | 13.3 | 2.3 | 74.0 | 6.6 | 0.2 | 2.3 | 12.9 | −2.5 | *32.0* |
| 29 | 2 | *67.2* | 15.3 | 2.4 | 73.2 | 5.8 | 0.1 | 0.5 | 4.9 | 1.1 | 14.1 |
| 30 | 2 | *66.6* | 13.8 | 2.3 | 70.5 | 8.3 | 0.5 | 0.7 | 8.3 | −2.6 | *30.6* |
| 31 | 2 | *65.9* | 12.1 | 2.8 | 69.9 | 6.7 | 0.6 | *4.3* | *21.4* | *−9.3* | *61.9* |
| 32 | 2 | *64.9* | 12.3 | 1.6 | 71.4 | 4.9 | 0.8 | 0.7 | 9.2 | −5.1 | *25.9* |
| 33 | 2 | *64.4* | 13.5 | 1.7 | 74.7 | 5.7 | 0.4 | 0.5 | 2.5 | −3.5 | *19.6* |
| 34 | 2 | *63.5* | 11.6 | 2.8 | 72.0 | 6.3 | 0.5 | 2.8 | *18.9* | −4.6 | *54.8* |
| 35 | 2 | *63.3* | 14.8 | 1.9 | 71.8 | 6.7 | 0.4 | 1.4 | 4.4 | 3.8 | *34.9* |

TABLE 3B-continued

Group 2 FT-NIR analysis of EVOO samples with potential adulteration

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 36 | 2 | *62.1* | 14.4 | 2.0 | 71.7 | 7.1 | 0.6 | *5.2* | *24.4* | *−4.2* | *68.1* |
| 37 | 2 | *61.0* | 13.6 | 2.1 | 71.1 | 7.3 | 0.5 | *2.5* | *17.4* | *−0.4* | *49.3* |
| 38 | 2 | *60.9* | 12.8 | 2.7 | 73.7 | 7.0 | 1.4 | *4.4* | *23.0* | *−6.6* | *58.3* |
| 39 | 2 | *58.1* | 13.9 | 1.4 | 73.1 | 8.3 | 0.5 | *4.6* | *22.7* | *−3.1* | *75.0* |
| 40 | 2 | *52.2* | 14.0 | 2.5 | 71.9 | 7.1 | 0.6 | *1.3* | *12.7* | *−1.7* | *41.1* |
| 41 | 2 | *51.1* | 14.9 | 2.3 | 67.5 | 8.2 | −0.3 | *2.6* | *11.9* | *0.5* | *49.9* |
| 42 | 2 | *48.8* | 11.8 | 1.7 | 75.6 | 4.5 | 1.3 | *6.3* | *26.8* | *−11.9* | *87.6* |
| 43 | 2 | *48.5* | 13.1 | 2.1 | 69.7 | 7.4 | 0.6 | *4.4* | *25.0* | *−4.1* | *83.3* |
| 44 | 2 | *40.7* | 12.4 | 2.2 | 72.7 | 6.7 | 0.6 | *4.0* | *21.3* | *−0.7* | *84.0* |

TABLE 4A

Group 3 FT-NIR analysis of EVOO samples for quality and purity

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 3 | 115.8 | 14.67 | 2.9 | 58.6 | 13.4 | 0.3 | −0.4 | −4.5 | 0.7 | −4.4 |
| 2 | 3 | 114.7 | 14.9 | 3.1 | 61.4 | 14.6 | −0.2 | 0.3 | 1.6 | 1.3 | −7.5 |
| 3 | 3 | 113.9 | 14.45 | 2.6 | 62.7 | 13.0 | 0.6 | −0.8 | −8.5 | 0.0 | −1.7 |
| 4 | 3 | 112.4 | 15.51 | 2.9 | 56.7 | 14.5 | 0.9 | 0.8 | −4.1 | −2.7 | −13.7 |
| 5 | 3 | 110.9 | 13.74 | 3.4 | 59.5 | 13.5 | 0.7 | −0.5 | −0.6 | −1.0 | 2.6 |
| 6 | 3 | 109.0 | 14.83 | 2.5 | 58.7 | 14.8 | 0.4 | 0.3 | −1.6 | 0.8 | −9.2 |
| 7 | 3 | 107.9 | 14.05 | 3.1 | 63.4 | 12.9 | 1.7 | −1.2 | −9.7 | 2.9 | −8.6 |
| 8 | 3 | 106.4 | 16.5 | 3.1 | 6.3 | 12.7 | 0.7 | −3.6 | −0.1 | 4.6 | 18.8 |
| 9 | 3 | 105.1 | 14.25 | 3.4 | 63.6 | 11.3 | 0.7 | −1.2 | −1.6 | −0.9 | 4.0 |
| 10 | 3 | 103.9 | 16.51 | 2.8 | 58.4 | 13.7 | 0.1 | 1.1 | 0.6 | −2.7 | −21.6 |
| 11 | 3 | 102.9 | 14.65 | 2.7 | 64.1 | 12.2 | 0.2 | −1.2 | 1.6 | −2.6 | 5.4 |
| 12 | 3 | 101.4 | 13.17 | 2.9 | 59.0 | 13.5 | −0.3 | −1.2 | −4.6 | 1.0 | 9.2 |
| 13 | 3 | 100.5 | 12.96 | 2.1 | 68.7 | 10.7 | 1.9 | −1.2 | −4.3 | 1.5 | 16.0 |
| 14 | 3 | 99.9 | 15.0 | 3.5 | 61.7 | 13.1 | 0.7 | 1.6 | 7.5 | −2.5 | −12.4 |
| 15 | 3 | 99.6 | 14.89 | 3.6 | 62.0 | 12.4 | 0.8 | −1.3 | −11.1 | 3.3 | 1.4 |
| 16 | 3 | 95.0 | 14.64 | 3.1 | 66.5 | 12.6 | 0.7 | −1.5 | −5.3 | −0.6 | 12.1 |
| 17 | 3 | 94.6 | 14.83 | 2.5 | 65.2 | 13.0 | 1.1 | −1.5 | −5.6 | 1.3 | 10.8 |
| 18 | 3 | 92.5 | 16.33 | 2.5 | 69.0 | 12.2 | 0.9 | −0.5 | −5.0 | 4.7 | 4.3 |
| 19 | 3 | 92.2 | 14.2 | 2.4 | 63.2 | 11.1 | 0.7 | 0.3 | 3.3 | −4.2 | −2.4 |
| 20 | 3 | 90.9 | 13.1 | 2.1 | 64.6 | 11.9 | 0.8 | 0.9 | 10.2 | −4.1 | 0.3 |
| 21 | 3 | 85.9 | 14.6 | 2.5 | 62.6 | 12.2 | 0.5 | 1.4 | 11.6 | −7.2 | −6.6 |
| 22 | 3 | 85.4 | 15.8 | 2.5 | 61.2 | 13.6 | 0.4 | 2.3 | 9.4 | −0.7 | −4.2 |
| 23 | 3 | 83.1 | 15.6 | 3.6 | 61.6 | 13.4 | 0.3 | 1.6 | 5.7 | −0.9 | −3.1 |
| 24 | 3 | 81.1 | 13.9 | 2.4 | 65.5 | 9.8 | 1.3 | 2.4 | 12.2 | −3.1 | −9.9 |
| 25 | 3 | 76.6 | 13.4 | 2.8 | 69.4 | 11.0 | 0.8 | 1.8 | 14.5 | 0.0 | 4.4 |
| 26 | 3 | 75.6 | 14.5 | 3.6 | 65.5 | 11.5 | 1.3 | 1.8 | 7.8 | 0.7 | −4.1 |

TABLE 4B

Group 3 FT-NIR analysis of EVOO samples with potential adulteration

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NTR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 3 | 89.1 | 17.3 | 3.7 | 50.8 | 17.9 | 1.0 | 6.3 | 8.2 | 2.4 | −68.0 |
| 2 | 3 | 87.0 | 9.9 | 0.8 | 70.9 | 10.2 | 1.3 | 5.2 | 37.1 | −12.6 | −26.0 |
| 3 | 3 | 86.1 | 15.0 | 3.7 | 59.0 | 15.3 | 0.2 | 7.8 | 28.9 | −4.8 | −55.3 |
| 4 | 3 | 84.7 | 17.3 | 3.5 | 52.7 | 17.2 | 0.3 | 6.3 | 12.4 | 3.9 | −66.1 |
| 5 | 3 | 83.2 | 12.1 | 2.1 | 73.8 | 10.0 | 0.8 | 3.8 | 32.8 | −12.7 | −17.9 |
| 6 | 3 | 80.5 | 15.7 | 3.0 | 57.9 | 14.7 | 0.2 | 5.1 | 17.7 | −0.5 | −40.3 |
| 7 | 3 | 80.3 | 15.2 | 3.0 | 61.2 | 13.9 | 0.7 | 3.8 | 11.9 | 2.8 | −19.1 |
| 8 | 3 | 80.2 | 14.7 | 3.0 | 61.7 | 12.4 | 0.2 | 3.2 | 8.7 | 1.5 | −19.0 |
| 9 | 3 | 79.1 | 12.6 | 2.5 | 62.0 | 18.4 | 1.4 | 18.9 | 83.7 | −20.8 | −143.2 |
| 10 | 3 | 77.3 | 18.5 | 3.3 | 51.6 | 19.4 | −0.2 | 8.1 | 21.2 | 0.4 | −73.6 |
| 11 | 3 | 76.5 | 15.9 | 3.1 | 60.7 | 14.3 | 0.5 | 5.5 | 22.0 | 0.0 | −28.4 |
| 12 | 3 | 75.4 | 13.8 | 3.1 | 66.1 | 14.7 | 1.4 | 8.7 | 40.6 | −7.2 | −61.3 |
| 13 | 3 | 73.0 | 10.7 | 1.7 | 71.9 | 0.2 | 0.6 | 1.9 | 26.6 | −5.6 | 5.8 |
| 14 | 3 | 71.6 | 13.6 | 2.3 | 67.1 | 11.8 | 0.3 | 2.1 | 14.7 | 1.0 | 4.6 |
| 15 | 3 | 70.7 | 15.9 | 2.8 | 59.1 | 14.4 | 1.8 | 7.6 | 25.3 | −1.2 | −53.9 |
| 16 | 3 | 69.6 | 14.1 | 2.7 | 66.3 | 11.3 | 0.6 | 2.8 | 18.7 | −3.8 | 0.4 |
| 17 | 3 | 68.7 | 12.1 | 3.0 | 67.6 | 10.6 | 1.1 | 1.7 | 18.2 | −6.9 | 12.5 |
| 18 | 3 | 67.2 | 15.4 | 3.1 | 60.9 | 13.5 | 0.7 | 8.0 | 33.8 | −3.4 | −50.7 |
| 19 | 3 | 65.4 | 12.3 | 1.7 | 64.6 | 9.1 | 1.4 | 6.3 | 38.0 | −9.5 | −31.8 |
| 20 | 3 | 63.2 | 12.0 | 2.3 | 70.1 | 8.1 | 1.4 | 3.2 | 30.2 | −9.9 | 4.0 |
| 21 | 3 | 58.7 | 13.7 | 3.7 | 63.6 | 11.1 | 0.7 | 3.7 | 19.4 | 1.6 | −8.1 |
| 22 | 3 | 58.5 | 14.0 | 2.5 | 59.4 | 12.4 | 0.4 | 2.0 | 10.8 | −4.2 | 6.7 |
| 23 | 3 | 55.2 | 15.8 | 3.0 | 62.2 | 13.3 | 1.0 | 6.3 | 26.4 | 4.1 | −36.3 |
| 24 | 3 | 52.8 | 12.1 | 2.0 | 69.4 | 8.8 | 2.1 | 5.4 | 31.0 | −7.9 | −11.8 |
| 25 | 3 | 52.0 | 15.4 | 3.6 | 59.1 | 13.9 | 0.3 | 4.2 | 14.3 | −0.1 | −11.3 |
| 26 | 3 | 51.8 | 16.0 | 2.5 | 62.7 | 12.1 | 0.8 | 2.8 | 15.8 | 1.6 | −8.6 |
| 27 | 3 | 50.8 | 7.7 | 2.0 | 58.6 | 23.2 | 6.0 | 54.0 | 229.8 | −64.6 | −450.4 |
| 28 | 3 | 50.3 | 8.3 | 3.1 | 28.6 | 55.2 | 3.6 | 106.0 | 428.1 | −123.4 | −913.0 |
| 29 | 3 | 48.6 | 14.9 | 2.6 | 60.2 | 11.9 | 0.4 | 2.6 | 9.2 | 3.0 | 2.1 |
| 30 | 3 | 47.9 | 15.9 | 2.3 | 59.2 | 14.6 | 1.2 | 7.5 | 28.6 | −0.8 | −39.8 |
| 31 | 3 | 47.0 | 15.6 | 2.8 | 61.1 | 12.1 | 0.8 | 2.5 | 14.3 | 0.6 | 12.4 |
| 32 | 3 | 44.5 | 8.1 | 2.3 | 32.6 | 53.5 | 3.5 | 100.6 | 411.4 | −114.7 | −852.9 |

TABLE 5A

Group 4 FT-NIR analysis of EVOO samples for quality and purity

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for preference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 4 | 90.3 | 13.3 | 1.8 | 73.1 | 2.6 | 0.4 | 0.6 | 0.6 | −1.4 | −5.7 |
| 2 | 4 | 78.0 | 11.0 | 1.7 | 75.0 | 1.5 | 0.2 | 0.7 | 3.3 | −2.8 | 2.3 |

TABLE 5B

Group 4 FT-NIR analysis of EVOO samples with potential adulteration

| | | | Predicted % FA (% of total FA) | | | | | Predicted % adulterant in EVOO | | | |
|---|---|---|---|---|---|---|---|---|---|---|---|
| | | | 16:0 | 18:0 | 18:1n-9 | 18:2n-6 | 18:3n-3 | Model 1 (LA) | Model 2 (OA) | Model 3 (PO) | Model 4 (RO) |
| | IDENT | FT-NIR | | | Standard IOC Range, % | | | | Mean ± 2SD for reference EVOO | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 1 | 4 | 91.7 | 12.0 | 1.9 | 73.3 | 5.0 | 0.1 | 3.5 | 11.1 | −9.8 | 12.4 |
| 2 | 4 | 81.1 | 12.4 | 1.5 | 73.1 | 4.2 | 1.1 | 3.0 | 11.4 | −1.2 | 29.7 |
| 3 | 4 | 80.3 | 15.6 | 2.0 | 72.4 | 3.8 | 1.3 | 1.5 | 4.8 | 4.4 | 20.5 |
| 4 | 4 | 79.2 | 12.6 | 2.5 | 73.6 | 5.2 | −0.3 | 2.4 | 12.2 | −4.0 | 27.6 |
| 5 | 4 | 74.3 | 14.0 | 2.1 | 77.6 | 4.5 | 0.0 | 2.2 | 12.6 | −6.0 | 20.5 |
| 6 | 4 | 73.5 | 13.1 | 2.7 | 73.7 | 2.2 | 1.3 | 3.8 | 12.2 | −1.8 | 29.1 |
| 7 | 4 | 73.0 | 13.0 | 2.2 | 76.5 | 3.3 | 1.1 | 2.9 | 9.7 | −0.5 | 24.0 |
| 8 | 4 | 65.1 | 13.3 | 2.1 | 76.3 | 1.3 | 0.9 | 0.6 | 2.2 | 4.1 | 9.0 |

TABLE 5B-continued

Group 4 FT-NIR analysis of EVOO samples with potential adulteration

| | | | Predicted % FA (% of total FA) | | | | Predicted % adulterant in EVOO | | | |
|---|---|---|---|---|---|---|---|---|---|---|
| | IDENT | FT-NIR | 16:0 | 18:0 | 18:1n-9 | 18:2n-6 | 18:3n-3 | Model 1 (LA) | Model 2 (OA) | Model 3 (PO) | Model 4 (RO) |
| | | | | Standard IOC Range, % | | | | Mean ± 2SD for reference EVOO | | | |
| Sample No. | Library | Index | 7.5-20 | 0.5-5.0 | 55-83 | 3.5-21 | 0-1.5 | (−2.3, 3.0) | (−8.4, 14.5) | (−7.6, 4.7) | (−22.4, 19.0) |
| 9 | 4 | 58.9 | 13.0 | 1.9 | 76.1 | 4.8 | 0.5 | 5.0 | 19.0 | −4.7 | 46.6 |
| 10 | 4 | 57.7 | 13.5 | 2.3 | 73.8 | 3.9 | 0.7 | 3.8 | 12.0 | 3.7 | 44.7 |
| 11 | 4 | 55.9 | 12.7 | 2.2 | 76.2 | 2.3 | 0.6 | 2.8 | 12.0 | 0.7 | 34.4 |
| 12 | 4 | 53.2 | 13.6 | 1.9 | 77.3 | 2.9 | 0.3 | 1.3 | 6.0 | 1.5 | 19.6 |
| 13 | 4 | 49.3 | 12.5 | 1.9 | 75.3 | 1.9 | 0.7 | 4.4 | 16.5 | −3.9 | 39.9 |
| 14 | 4 | 48.5 | 13.0 | 1.3 | 80.3 | 2.6 | 1.4 | 3.3 | 15.2 | −1.5 | 36.3 |

What is claimed is:

1. A method for the detection of adulteration in a test edible oil sample utilizing an FT-NIR analysis technique, comprising:
   A) conducting an FT-NIR spectroscopic analysis to determine an FT-NIR Index value for an edible oil sample by:
      (i) analysing an unadulterated, authentic edible oil sample using FT-NIR in order to determine the relative absorption by the authentic edible oil at two selected wave numbers, and thereby create an FT-NIR Index calibration model;
      (ii) conducting an FT-NIR spectroscopy analysis of an unknown edible oil sample and determining the relative absorption of said unknown oil sample at said two selected wave numbers; and,
      (iii) comparing, via a processor, the ratio of the relative absorption of said FT-NIR spectroscopy analysis of said unknown edible oil sample at the same two selected wave numbers, to said FT-NIR Index calibration model of said authentic edible oil, at the same selected wave numbers, in order to calculate said FT-NIR Index value; and
      (iv) reviewing said FT-NIR Index value, and if said FT-NIR Index value is below an accepted value, consider said test edible oil sample to be an adulterated oil sample,
   B) if said test oil sample is an adulterated oil sample, determine the type and/or quantity of adulteration of said test edible oil sample by:
      (v) preparing an FT-NIR calibration matrix, comprising a series of calibration models for at least two edible oil classifications, which classifications are established using a classification criteria, and which calibration models are based on FT-NIR analysis of authentic oils and authentic oils spiked with adulterants, for said classifications;
      (vi) conducting an FT-NIR spectroscopy analysis of said test edible oil sample;
      (vii) analysing said test edible oil sample using said classification criteria in order to determine and select the most suitable edible oil classification, and thereby determine the most suitable calibration models, for that test edible oil sample; and,
      (viii) comparing, via the processor, the FT-NIR spectroscopy analysis of said test edible oil sample, to said calibration models for said most suitable edible oil classifications, in order to determine the type and level of adulterant or adulterants present in said test edible oil sample.

2. A method as claimed in claim 1, wherein said test edible oil sample is an olive oil sample.

3. A method as claimed in claim 1, wherein said test edible oil sample is an extra virgin olive oil (EVOO) sample.

4. A method as claimed in claim 1, wherein said FT-NIR spectroscopy analysis is used to identify and quantify at least 1 adulterant present in said test oil sample.

5. A method as claimed in claim 4, where said FT-NIR spectroscopy analysis is used to identify and quantify between 1 and 6 adulterants present in said test oil sample.

6. A method as claimed in claim 1, wherein between 4 and 6 edible oil classification groups are established using said classification criteria.

7. A method as claimed in claim 1, wherein said FT-NIR analysis is conducted at wave numbers between the range of 4500 to 9000 $cm^{-1}$.

8. A method as claimed in claim 1 wherein the FT-NIR index is at its highest level of 100% when an authentic edible oil sample is tested, and wherein an accepted value for said FT-NIR Index for a test edible oil sample, is a value of above 75%.

9. A method as claimed in claim 8 wherein said accepted value for said FT-NIR Index for a test edible oil sample is a value of above 90%.

10. A method as claimed in claim 1 wherein said FT-NIR Index is calculated by using the following formula:

$$\text{FT-NIR Index} = [(\text{TS-ABS}_{5269}/\text{TS-ABS}_{5180})/(\text{Authentic-ABS}_{5269}/\text{Authentic-ABS}_{5180})] \times 100$$

where: TS-ABS is the absorbance for the test sample in the range centered at essentially the indicated wave numbers; and
Authentic-ABS is the absorbance for authentic EVOO sample in the range centered at essentially the indicated wave number values.

11. A method as claimed in claim 1 for determining whether an edible oil sample has been adulterated, comprising:
   conducting an FT-NIR spectroscopy analysis of said edible oil sample and determining an FT-NIR Index for the sample to be tested;
   reviewing said FT-NIR Index value, and if said FT-NIR Index value is below an accepted value, consider said test edible oil sample to be an adulterated oil sample;
   determining the fatty acid (FA) composition for the adulterated oil sample to be tested, and confirming that FA levels are within edible oil standards; and
   analyzing the levels in said adulterated oil sample of adulterant oils high in linoleic acid (LA), oleic acid (OA), palmitic acid (PO), or refined olive oil (RO), and selecting the appropriate classification matrix based on the fatty acid levels; and using the calibration models for the selected classification matrix, determine the levels of the adulterant oils present in ter the edible oil being analysed.

12. A method as claimed in claim 11 wherein said FT-NIR spectroscopy analysis additionally comprises determining the fatty acid (FA) composition for the test edible oil sample to be tested, and confirming that FA levels for said sample are within EVOO standards.

13. A method as claimed in claim 11 wherein said FT-NIR spectroscopy analysis additionally comprises determining the levels of adulterant oils high in linoleic acid (LA), Oleic acid (OA), Palmitic acid (PO), or refined olive oil (RO), using the calibration models for the selected classification, to determine that these levels are within accepted levels for the edible oil being analysed.

14. A method as claimed in claim 11 wherein said oil high in linoleic acid is corn oil, soybean oil, sunflower oil or canola oil, high in oleic acid (OA) is hazelnut oil, high oleic safflower, high oleic canola, high oleic sunflower, or peanut oil, or high in palmitic acid (PO) is palm olein.

15. A method as claimed in claim 1 wherein said FT-NIR calibration matrix is based on FT-NIR analysis of unadulterated oil, and unadulterated oils which have been spiked with up to 6 adulterants.

16. A method as claimed in claim 15 wherein said edible oil samples are classified into between 4 and 6 edible oil classifications, and wherein said edible oil sample is an adulterated EVOO sample.

17. A method as claimed in claim 1 wherein said FT-NIR analysis is used to determine both the type and level of adulterants.

18. A method as claimed in claim 1 wherein steps (ii) to (iv), and steps (vi) to (viii) are conducted for a plurality of test edible oil samples, once an FT-NIR Index calibration model and a FT-NIR calibration matrix have been prepared.

* * * * *